US009028797B2

(12) United States Patent
Sasaki et al.

(10) Patent No.: US 9,028,797 B2
(45) Date of Patent: May 12, 2015

(54) COMPOSITE BODY FOR ANTIGEN OR DRUG DELIVERY

(75) Inventors: Hitoshi Sasaki, Nagasaki (JP); Tomoaki Kurosaki, Nagasaki (JP); Takashi Kitahara, Nagasaki (JP); Hideto To, Nagasaki (JP); Katsuyuki Yui, Nagasaki (JP); Kenji Hirayama, Nagasaki (JP); Kouichi Morita, Nagasaki (JP); Takahiro Mukai, Kobe (JP); Yasuhiro Magata, Hamamatsu (JP); Mikako Ogawa, Hamamatsu (JP); Kohei Sano, North Bethesda, MD (US)

(73) Assignees: Nagasaki University, Nagasaki (JP); Kyusyu University Corporation, Fukuoka (JP); National University Corporation Hamamatsu University School of Medicine, Hamamatsu (JP)

( * ) Notice: Subject to any disclaimer, the term of this patent is extended or adjusted under 35 U.S.C. 154(b) by 177 days.

(21) Appl. No.: 13/581,194

(22) PCT Filed: Feb. 24, 2011

(86) PCT No.: PCT/JP2011/054195
§ 371 (c)(1),
(2), (4) Date: Nov. 6, 2012

(87) PCT Pub. No.: WO2011/105520
PCT Pub. Date: Sep. 1, 2011

(65) Prior Publication Data
US 2013/0052127 A1 Feb. 28, 2013

(30) Foreign Application Priority Data

Feb. 26, 2010 (JP) ................................. 2010-043186

(51) Int. Cl.
| A61K 49/00 | (2006.01) |
| A61K 51/06 | (2006.01) |
| A61K 31/711 | (2006.01) |
| A61K 31/713 | (2006.01) |
| A61K 39/00 | (2006.01) |
| A61K 39/015 | (2006.01) |
| A61K 39/145 | (2006.01) |
| A61K 39/39 | (2006.01) |
| A61K 47/48 | (2006.01) |

(52) U.S. Cl.
CPC ........... *A61K 49/0002* (2013.01); *A61K 31/711* (2013.01); *A61K 31/713* (2013.01); *A61K 39/0011* (2013.01); *A61K 39/015* (2013.01); *A61K 39/145* (2013.01); *A61K 39/39* (2013.01); *A61K 47/48192* (2013.01); *A61K 47/482* (2013.01); *A61K 51/065* (2013.01); *A61K 2039/5252* (2013.01); *A61K 2039/55555* (2013.01)

(58) Field of Classification Search
None
See application file for complete search history.

(56) References Cited

U.S. PATENT DOCUMENTS

| 5,338,532 A | 8/1994 | Tomalia et al. |
| 5,700,459 A | 12/1997 | Krone et al. |
| 5,855,913 A | 1/1999 | Hanes et al. |
| 7,056,532 B1 | 6/2006 | Kabanov et al. |
| 2001/0005717 A1 | 6/2001 | Wagner et al. |
| 2003/0165478 A1 | 9/2003 | Sokoll |
| 2005/0118201 A1 | 6/2005 | Wright et al. |
| 2005/0266065 A1 | 12/2005 | Perrier et al. |
| 2006/0252717 A1 | 11/2006 | Barenholz et al. |
| 2008/0063701 A1 | 3/2008 | Keller et al. |
| 2008/0311182 A1 | 12/2008 | Ferrari et al. |
| 2009/0053299 A1 | 2/2009 | Chang et al. |
| 2009/0123467 A1 | 5/2009 | Bedi et al. |
| 2010/0172930 A1 | 7/2010 | Hart et al. |

FOREIGN PATENT DOCUMENTS

| EP | 0 640 347 A1 | 3/1995 |
| JP | S63-501876 A | 7/1988 |
| JP | H03-106896 A | 5/1991 |
| JP | H04-046129 A | 2/1992 |
| JP | H04-225915 A | 8/1992 |
| JP | H05-339169 A | 12/1993 |
| JP | H10-511957 A | 11/1998 |
| JP | 2000-501381 A | 2/2000 |
| JP | 2001-302541 A | 10/2001 |
| JP | 2001-340752 A | 12/2001 |
| JP | 2001-526634 A | 12/2001 |
| JP | 2002-504123 A | 2/2002 |
| JP | 2002-506441 A | 2/2002 |
| JP | 2004-532197 A | 10/2004 |

(Continued)

OTHER PUBLICATIONS

Kobayashi et al. Delivery of gadolinium-labeled nanoparticles to the sentinel lymph node: comparison of the sentinel node visualization and estimations of intra-nodal gadolinium concentration by the magnetic resonance imaging. 2006 J. Control. Release 111: 343-351.*

(Continued)

*Primary Examiner* — Michael G Hartley
*Assistant Examiner* — Jennifer Lamberski
(74) *Attorney, Agent, or Firm* — Leydig, Voit & Mayer, Ltd.

(57) ABSTRACT

The invention provides an antigen or drug delivery complex containing a complex of an antigen or drug and a cationic molecule, and an anionic molecule encapsulating the same. The antigen or drug delivery complex can be used as a main component of a drug delivery system that delivers various antigens and drugs to a particular cell or organ.

5 Claims, 25 Drawing Sheets

(56) References Cited

FOREIGN PATENT DOCUMENTS

| | | |
|---|---|---|
| JP | 2005-530690 A | 10/2005 |
| JP | 2005-535633 A | 11/2005 |
| JP | 2005-350445 A | 12/2005 |
| JP | 2005-538923 A | 12/2005 |
| JP | 2006-028041 A | 2/2006 |
| JP | 2006-527762 A | 12/2006 |
| JP | 2008-509205 A | 3/2008 |
| JP | 2008-247855 A | 10/2008 |
| JP | 2010-059064 A | 3/2010 |
| JP | 2010-173990 A | 8/2010 |
| WO | 96/20698 A1 | 7/1996 |
| WO | 97/14442 A1 | 4/1997 |
| WO | 2004/002454 A1 | 1/2004 |
| WO | 2008/021908 A2 | 2/2008 |
| WO | 2008/041703 A1 | 4/2008 |
| WO | 2009/009054 A1 | 1/2009 |
| WO | 2009/018500 A1 | 2/2009 |

OTHER PUBLICATIONS

Kashiwagi et al., *Drug Delivery System*, 20(3): 369, Item p-44 (2005).
Koyama et al., *Journal of Magnetic Resonance Imaging*, 25: 866-871 (2007).
Kurosaki et al., *Drug Delivery System*, 24(3): 341, Item P-039 (2009).
Kurosaki et al., *Drug Delivery System*, 25(3): 334, Item P-45 (2010).
Kurosaki et al., *Biomaterials*, 30: 2846-2853 (2009).
Kurosaki et al., *Journal of Controlled Release*, 136: 213-219 (2009).
Kishikawa et al., *Drug Delivery System*, 23(3): 358, Item 29D-14 (2008).
Matsuo et al., *65$^{th}$ Annual Meeting of the Japan Cancer Association Yokoshu*, 321: Item P-665 (2006).
International Bureau of WIPO, International Preliminary Report on Patentability in International Patent Application No. PCT/JP2011/054195 (Nov. 7, 2012).
Japanese Patent Office, International Search Report in International Patent Application No. PCT/JP2011/054195 (Apr. 26, 2011).

* cited by examiner

FIG. 4
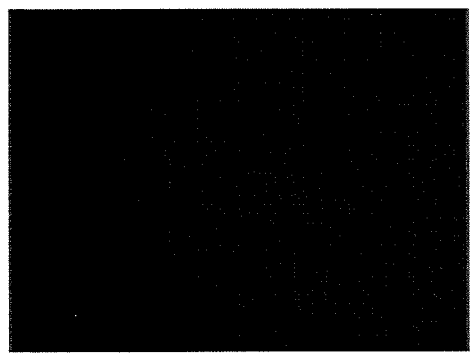 
BSA alone　　　BSA/BAC/γ-PGA

FIG. 10
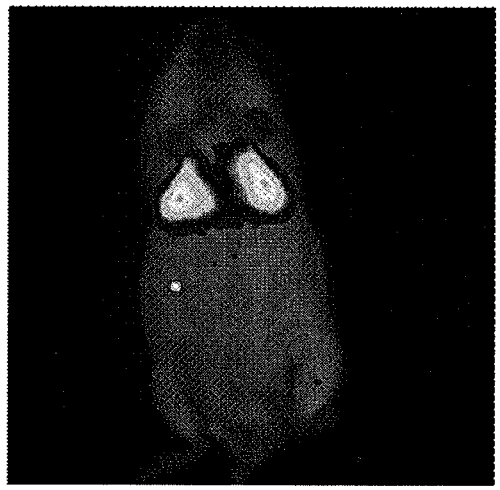 
1:2:2:2                                    1:8:0:0

FIG. 17
dendritic cell line (DC2.4)
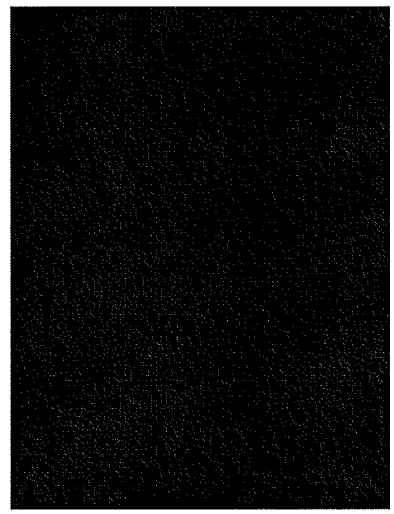 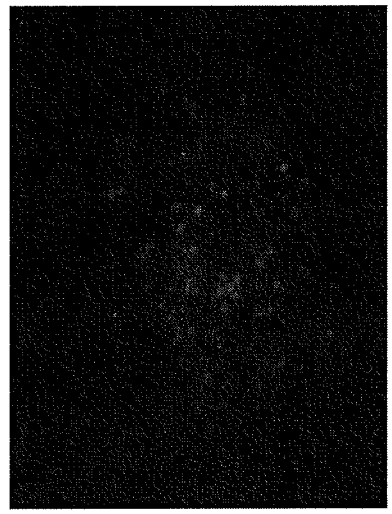
Inactivated influenza vaccine    Vaccine/BAC/$\gamma$-PGA

COMPOSITE BODY FOR ANTIGEN OR DRUG DELIVERY

CROSS-REFERENCE TO RELATED APPLICATIONS

This patent application is a U.S. national phase of International Patent Application PCT/JP2011/054195, filed on Feb. 24, 2011, which claims the benefit of Japanese Patent Application No. 2010-043186, filed on Feb. 26, 2010, which are incorporated by reference in their entireties herein.

TECHNICAL FIELD

The present invention relates to a novel antigen delivery complex, a vaccine, a drug delivery complex and the like.

BACKGROUND ART

In recent years, inactivated vaccines and attenuated vaccines were developed for emerging or reemerging infections, and high prophylaxis effects have been obtained. However, the development of vaccine against infections is far behind in Japan. For eradication of particular infection and dealing with pandemic in the developing countries, the development of a vaccine permitting large-scale production and long-term preservation, and having high safety and strong titer has been desired. Among others, a DNA vaccine permitting large-scale production at a low cost is expected to prove effective; however, the development thereof is not successful from the aspects of safety and titer. In addition, the development of a preparation suitable for intravenous injection, subcutaneous or intradermal injection that activates body immunity, and a preparation suitable for oral, inhaled or nasal administration that activates mucosal immunity is necessary.

Moreover, it has been reported that a vaccine against human papilloma virus has been approved as a cervical cancer vaccine and shows a high effect. However, a vaccine therapy of cancer antigen has not been established as yet in the world. While vaccines using various antigens and DNAs have been reported, a sufficient immunity induction effect was not obtained and clinical application has not been commenced. Particularly, DNA vaccine is expected to selectively activate cellular immunity relating to cancer, and potentiate the anticancer immunity. While DNA vaccine is drawing attention since it permits large-scale production at a low cost, there is no successful case in terms of safety and titer.

Since DNA pharmaceutical products show different pharmacological actions by changing the combination of bases and permit large-scale production at a low cost, they are expected to prove effective as pharmaceutical products. Heretofore, various nanostructures have been developed as a vector for gene delivery, and their organ specificity and cell specificity have been reported. However, since safety and efficiency are low, they have not been put to clinical use. Since many of them use synthetic materials, safety has not been established and the medical economy is large. The development of an organ specific vector having high safety and broad utility has been desired.

There are some methods to make a vector organ specific, one of which is a method using a particular molecule that easily accumulates in a target organ, and the other is a method using a molecule having a specific binding ability, which is an antibody, an aptamer and the like.

As the former method, the present inventors have succeeded in the construction of a novel targeting system having selectivity to the spleen and the lung, by applying the technique of a drug delivery complex (patent document 1) and conveniently adding a biodegradable lipid. To be specific, the safety of nanoparticles was enhanced by a simple addition of phosphatidylserine (negative charge) to a cationic nucleus encapsulating a DNA, and gene expression selective only to the spleen could be realized by intravenous injection to a mouse. The spleen contains an abundance of immunocytes, and a spleen-selective gene expression leads to the development of DNA vaccine. Furthermore, the addition of N-lauroylsarcosine (negative charge) instead of phosphatidylserine resulted in the gene expression only in the lung after its intravenous injection to a mouse and enhanced the safety of nanoparticles (non-patent document 1).

DOCUMENT LIST

Patent Document patent document 1: JP-A-2010-059064

Non-Patent Document non-patent document 1: Journal of Controlled Release, 136, 213-219 (2009)

SUMMARY OF THE INVENTION

Problems to be Solved by the Invention

The problem of the present invention is to provide an antigen delivery complex, a vaccine, a drug delivery complex and the like, which are safe, have a high titer, and permit large-scale production and preservation. Particularly, the problem is to provide a cell- or organ-oriented antigen or a cell- or organ-oriented drug delivery complex.

Means of Solving the Problems

The present inventors have conducted intensive studies in an attempt to solve the aforementioned problems and found that a complex of the DNA of a malaria antigen and a cationic molecule, which is coated with an anionic molecule of any of γ-polyglutamic acid, chondroitin sulfate and alginic acid, substantially is not electrically charged or has a negative surface charge, shows low cytotoxicity, does not cause red blood cell agglutination, shows high transfection efficiency in various cells, and further, can efficiently deliver an antigen DNA to the spleen by in vivo systemic administration.

In addition, they have found that an antibody specific to malaria can be produced by multiple administrations, and thereby malaria infection can be suppressed. Furthermore, they have found that malignant melanoma-specific cellular immunity can be induced when a pDNA encoding a surface antigen of malignant melanoma is used as a cancer antigen, and the growth and the metastasis of malignant melanoma can be suppressed.

In addition, the present inventors have succeeded in the production of a complex, which is substantially not electrically charged or has a negative surface charge, by coating a complex of an inactivated virus or cancer antigen and a cationic molecule with an anionic molecule of any of γ-polyglutamic acid, chondroitin sulfate and alginic acid. Moreover, they have found that the obtained vaccine can be successfully delivered into the dendritic cell, and shows a high immunity induction effect when administered to an experimental animal.

Furthermore, the present inventors have succeeded in the construction of a novel targeting system that enables cell or organ-specific delivery, by applying the technique described in patent document 1. That is, they have succeeded in the development of a complex of an antigen or drug and a cationic molecule, and an antigen or drug delivery complex containing an anionic molecule encapsulating the same and oriented to a cell or organ.

In addition, they have also succeeded in the production of an antigen or drug delivery complex imparted with the selectivity (organ selectivity) each to the spleen, lung or liver, by the addition of an anionic molecule selected from phosphatidylserine, N-lauroylsarcosine and glycyrrhizin to a complex of an antigen or drug and a cationic molecule.

Furthermore, they have found a dendritic cell-oriented complex can be produced by using γ-polyglutamic acid as an anionic molecule.

It has been clarified that these complexes have extremely high safety and no cytotoxicity since a complex of an antigen or drug and a cationic molecule, and an anionic molecule are electrostatically bound.

In addition, they have also succeeded in the production of a complex imparted with more specific cell or organ selectivity by further addition of an anionic molecule selected from an aptamer, miRNA and an antibody to a complex of an antigen or drug and a cationic molecule.

Additionally, they have also succeeded in using the above-mentioned complex as a carrier for delivering a nuclide for imaging (imaging probe) or diagnostic reagent to a particular cell or organ, by using a known nuclide for imaging (imaging probe) or a diagnostic reagent as an antigen or drug.

Accordingly, the present invention provides the following.

[1] An antigen or drug delivery complex, comprising a complex of an antigen or drug and a cationic molecule, and an anionic molecule encapsulating the same, which is cell- or organ-oriented.
[2] The complex according to [1], wherein the antigen or drug is a nucleic acid, a peptide, a protein or an inactivated virus.
[3] The complex according to [1] or [2], wherein the anionic molecule is selected from phosphatidylserine, lauroylsarcosine and glycyrrhizin, which is spleen-, lung- or liver-oriented.
[4] The complex according to [3], wherein the anionic molecule is phosphatidylserine, which has a mixing ratio of the antigen or drug, cationic molecule, phosphatidylserine of 1:2:4-1:8:8 and is spleen-oriented.
[5] The complex according to [3], wherein the anionic molecule is lauroylsarcosine and the cationic molecule consists of a cationic polymer and a cationic lipid, which has a mixing ratio of the antigen or drug, cationic polymer, cationic lipid, lauroylsarcosine of 1:2:2:1-1:2:2:4 and is lung-oriented.
[6] The complex according to [3], wherein the anionic molecule is glycyrrhizin, which has a mixing ratio of the antigen or drug, cationic molecule, glycyrrhizin of 1:2:8-1:8:16 and is liver-oriented.
[7] The complex according to [1] or [2], wherein the anionic molecule is γ-polyglutamic acid, which is dendritic cell- or spleen-oriented.
[8] The complex according to [7], which has a mixing ratio of the antigen or drug, cationic molecule, γ-polyglutamic acid of 1:2:8-1:8:16 and is dendritic cell- or spleen-oriented.
[9] The complex according to [1] or [2], wherein the anionic molecule is selected from an aptamer, miRNA and an antibody.
[10] The complex according to [9], wherein the mixing ratio of the antigen or drug, cationic molecule, anionic molecule is 1:2:8-1:8:16.
[11] The complex according to any one of [1] to [10], wherein the complex is constituted with an antigen or drug; a cationic polymer selected from polylysine, polyarginine, polyhistidine, polyethylenimine and cationic dendrimer, or a cationic lipid selected from DOTMA, DOTAP, DC-Chol and benzalkonium chloride.
[12] The complex according to any one of [1] to [10], which is constituted with an antigen or drug; and liposome or micelle made from a cationic lipid selected from DOTMA, DOTAP and DC-Chol and a lipid selected from DOPE and cholesterol.
[13] A carrier of a nuclide for imaging, comprising the complex according to any one of claims 1 to 12.
[14] The carrier according to [13], wherein the antigen or drug is a complex consisting of a nuclide for imaging, a cationic dendrimer and a chelating agent;
the cationic molecule is polyethylenimine; and
the anionic molecule is γ-polyglutamic acid; which is lymph node-oriented.
[15] A method of imaging sentinel lymph node, comprising using a complex constituted with a complex consisting of a nuclide for imaging, a cationic dendrimer and a chelating agent; polyethylenimine; and γ-polyglutamic acid.
[1'] An antigen delivery complex comprising a complex of an antigen and a cationic molecule and an anionic molecule encapsulating the same, which substantially has no electric charge or has negative surface charge, wherein the anionic molecule is selected from the group consisting of γ-polyglutamic acid, chondroitin sulfate, alginic acid and a salt thereof.
[2'] The complex according to [1'], wherein the antigen is a pathogen's antigen or a DNA encoding the same.
[3'] The complex according to [2'], wherein the pathogen is a malaria parasite.
[4'] The complex according to [2'], wherein the antigen is an inactivated virus.
[5'] The complex according to [4'], wherein the virus is an influenza virus, a hepatitis virus, a SARS virus, a papilloma virus, or an HIV virus.
[6'] The complex according to [1'], wherein the molar ratio of a positively-charged functional group of the cationic molecule and a negatively charged functional group of the anionic molecule is 3:1-1:4.
[7'] The complex according to [1'], wherein the anionic molecule has a molecular weight of not more than 100,000.
[8'] The complex according to [1'], wherein the anionic molecule is γ-polyglutamic acid or a salt thereof.
[9'] The complex according to [1'], wherein the cationic molecule is polyethylenimine, benzalkonium chloride, N-[1-(2,3-dioleyl oxy)propyl]-N,N,N-trimethylammonium or a salt thereof.
[10'] The complex according to [8'], which is used for delivering an antigen to the spleen.
[11'] A vaccine for infection, comprising the complex according to any one of [1']-[10'].
[12'] The vaccine according to [11'], wherein the infection is malaria infection or virus infection.
[13'] A method of delivering an antigen into a dendritic cell, comprising contacting the complex according to any one of [1']-[10'] or the vaccine according to [11'] or [12'] with the cell.
[14'] A method of delivering an antigen into a cell of a mammal, comprising administering the complex according to any one of [1']-[10'] or the vaccine according to [11'] or [12'] to the mammal.
[15'] A drug delivery complex comprising a liposome comprising a complex of a drug and a cationic molecule, and an anionic molecule encapsulating the same, which complex substantially having no electric charge or having negative surface charge, and the anionic molecule is selected from the group consisting of lauroylsarcosine and phosphatidylserine.

[16'] The complex according to [15'], which is used for delivering a drug to the spleen.

[17'] The complex according to [15'], which is used for delivering a drug to the lung.

[18'] The complex according to [15'], wherein the liposome comprises a drug, a cationic molecule and a cationic lipid.

[19'] The complex according to [18'], wherein the cationic molecule is polyethylenimine and the cationic lipid is N-[1-(2,3-dioleyl oxy)propyl]-N,N,N-trimethylammonium.

[20'] The complex according to any one of [1'] and [6']-[10'], wherein the antigen is a cancer antigen or a DNA encoding the same.

[21'] A cancer vaccine comprising the complex [20'].

[22'] The vaccine according to [21'] wherein the cancer is malignant melanoma.

[23'] A method of delivering an antigen into a dendritic cell, comprising contacting the complex according to [20'] or the vaccine according to [21'] or [22'] with the dendritic cell.

[24'] A method of delivering an antigen into a cell of a mammal, comprising administering the complex according to [20'] or the vaccine according to [21'] or [22'] to the mammal.

[25'] An organ-specific drug delivery complex comprising a complex of a drug and a cationic molecule, an antibody encapsulating the same, an aptamer or a salt thereof, wherein the antibody, the aptamer or the salt thereof are electrostatically bound to the complex of the drug and the cationic molecule.

[26'] A method of delivering a drug into a specific cell, comprising delivering the drug delivery complex according to [25'] to the specific cell.

[27'] A method of delivering a drug into a specific cell of a mammal, comprising administering the drug delivery complex according to [25'] to the animal.

[28'] The drug delivery complex of [15'] or [25'], wherein the drug is a negatively-charged nucleic acid such as DNA, siRNA, miRNA, antisense DNA and the like.

Effect of the Invention

The complex of the present invention does not cause red blood cell agglutination, shows low cytotoxicity, and is superior in the cellular uptake efficiency, it can deliver an antigen or drug safely and effectively.

Particularly, since the complex of the present invention is characteristically highly oriented to the target cell or organ, it can be an active ingredient of a new drug delivery system.

BRIEF DESCRIPTION OF THE DRAWINGS

FIG. 4 shows fluorescence microscopic observation images after addition of the complex to the cells in Example 3.

FIG. 10 shows mouse images by luciferase imaging in Example 5.

FIG. 17 shows uptake of inactivated virus by dendritic cell lines in Example 9.

DESCRIPTION OF EMBODIMENTS

Figure 1:
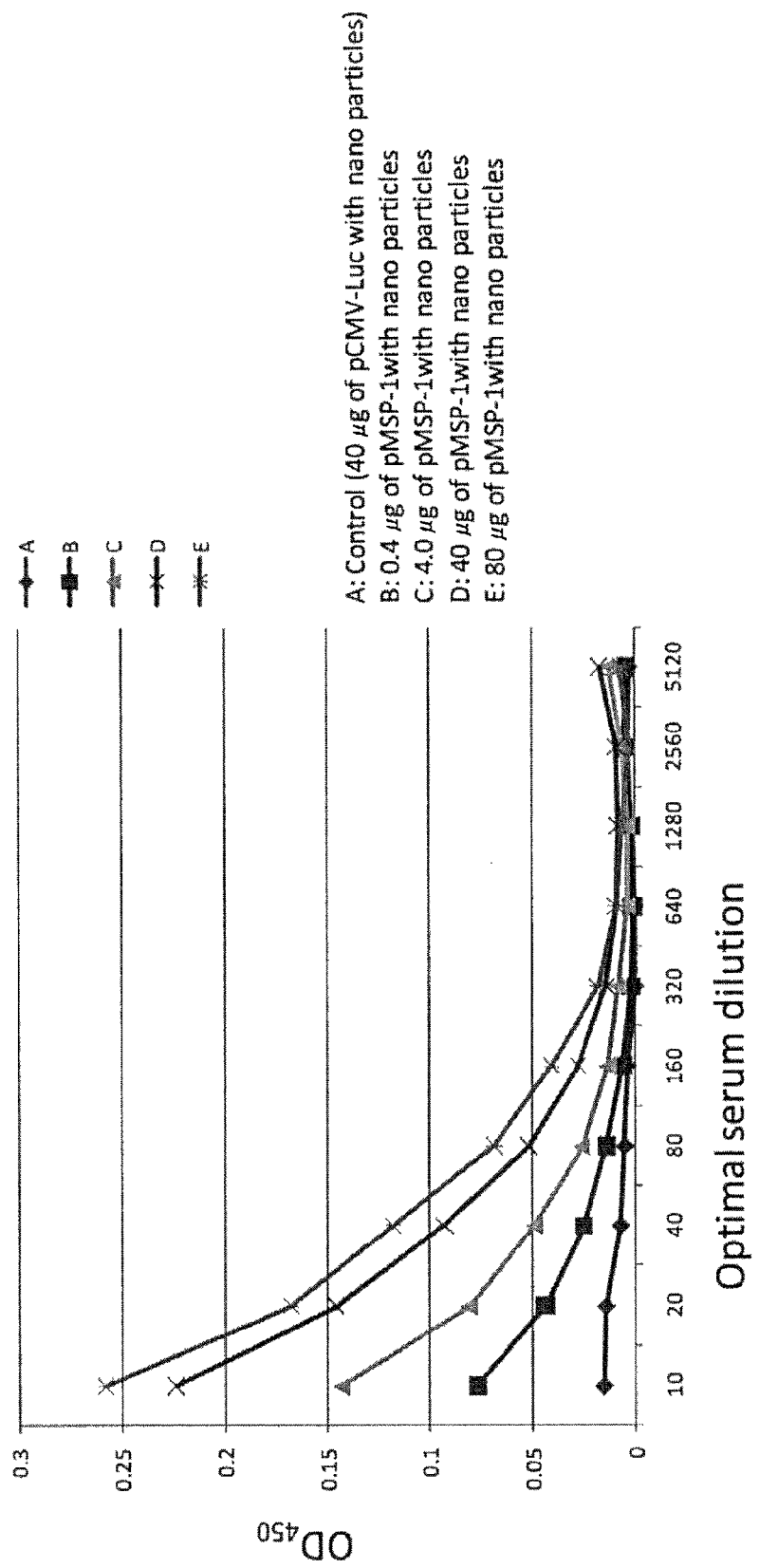
FIG. 1 shows vaccine antibody titers in Example 1.

The present invention provides an antigen or drug complex to deliver an antigen into a desired cell or organ (hereinafter to be also referred to as the "antigen delivery complex of the present invention", "drug delivery complex of the present invention", or collectively, "the complex of the present invention").

The antigen delivery complex of the present invention and the drug delivery complex of the present invention are each explained below.

The "antigen delivery complex of the present invention" comprises a complex of an antigen and a cationic molecule, and an anionic molecule encapsulating the same, and is characteristically cell- or organ-oriented.

Examples of the "antigen" in the antigen delivery complex of the present invention include pathogen's antigen (particularly surface antigen of pathogens) or a DNA encoding same, and inactivated virus.

In the pathogen antigen, the "pathogen" to be interested in includes various pathogens for which a vaccine therapy is desired, since, as mentioned below, the antigen delivery complex of the present invention is used as a vaccine. Specifically, malaria parasite, influenza virus, hepatitis virus, West Nile virus, HIV virus (human immunodeficiency virus), papilloma virus, SARS (severe acute respiratory syndrome) virus and the like can be mentioned.

Such pathogen antigen is selected from surface antigens (e.g., protein (antigen), peptide (antigen) and the like) of the pathogens and nucleic acid (e.g., DNA) antigens encoding same and the like.

While the kind of the nucleic acid in the aforementioned nucleic acid antigen can be appropriately selected according to the object of use and is not particularly limited, it includes plasmid DNA (pDNA), cDNA, antisense DNA, siRNA, miRNA, chromosomal DNA, PAC, BAC and the like can be mentioned, with preference given to plasmid DNA, cDNA, antisense DNA. The circular DNA such as plasmid DNA and the like is appropriately digested with a restriction enzyme and the like, also permitting use as a linear DNA.

While the size of the nucleic acid is not particularly limited, it is 2-15 kbp, preferably 2-10 kbp, more preferably 4-10 kbp, in the case of a plasmid DNA. In addition, a 1-5 kbp DNA is also preferable.

The nucleic acid may be any of naturally-occurring one and synthesized one, and a nucleic acid having a size of about 100 bp or below can be synthesized by an automatic nucleic acid synthesizer generally used according to a phosphotriethyl method, a phosphodiester method and the like.

A nucleic acid having a larger size can be appropriately prepared by a method generally used.

While the nucleic acid used in the present invention is not particularly limited; it is preferably purified by a method generally used by those of ordinary skill in the art.

As the antigen in the present specification, a surface antigen of the pathogen or a nucleic acid encoding same as mentioned above, as well as the pathogen (virus) per se can be used. In this case, an inactivated virus is used for protection against infection.

As the inactivated virus, any can be used as long as it is obtained by a generally-employed method. For example, formalin treatment, UV irradiation, β-propiolactone and the like can be used.

As such antigen, preferred are a nucleic acid, a peptide, a protein and an inactivated virus. One embodiment thereof is, for example, a malaria antigen gene, an inactivated influenza virus or the like.

Another embodiment of the present invention is an antigen delivery complex obtained by using, as an antigen, a cancer antigen or a DNA encoding the same. Since a cancer antigen is used as an antigen, the antigen is preferably delivered in a cell-specific manner. In other words, a specific delivery of an antigen to an antigen presenting cell such as dendritic cell and the like is expected to provide a high immunity induction effect.

The above-mentioned antigen may form, together with the below-mentioned drug of the present invention, the complex of the present invention. Therefore, the antigen delivery complex of the present invention may be an antigen delivery complex incorporating a drug.

On the other hand, the "drug delivery complex" of the present invention comprises a complex of a drug and a cationic molecule, and an anionic molecule encapsulating the same, and is cell- or organ-oriented.

The "drug" in the drug delivery complex of the present invention may be any and, for example, nucleic acid, peptide, protein, lipid, peptide lipid, sugar, low-molecular-weight compound, other synthetic or natural compound and the like can be mentioned. These compounds may contain various nuclides (e.g., natural radioactive nuclide, artificial radioactive nuclide, positron-emitting release nuclide and the like), or radiolabeled with a nuclide. Alternatively, it may be labeled with various compounds (e.g., known fluorescent dye, enzyme and the like). The drug may be only one kind, or two or more kinds.

When drug delivery into a cell or organ by the drug delivery complex of the present invention aims at the treatment and/or prophylaxis of a disease, the drug has a therapeutic and/or prophylactic activity for a disease. Examples thereof include any capable of acting as antihypertensive agent, antihypotensive agent, antipsychotic agent, analgesic, antidepressant, antimanic agent, anti-anxiety agent, abirritant, hypnotic, antiepileptic agent, opioid agonist, asthma therapeutic agent, anesthetic, antiarrhythmic agent, arthritistherapeutic agent, anticonvulsive agent, ACE inhibitor, decongestant, antibiotic, antianginal agent, diuretic, antiparkinsonian agent, bronchodilating agent, oxytocic agent, antidiuretic, antilipidemic agent, immunosuppressant, immune-regulating agent, antiemetic agent, anti-infective agent, antineoplastic agent, antifungal agent, antiviral agent, antidiabetic agent, antiallergic agent, antifebrile, antitumor agent, antigout agent, antihistamine agent, antipruritic agent, bone-regulating agent, cardiovascular agent, hypocholesterolemic agent, antimalarial agent, medicament to stop smoking, antitussive agent, expectorant, mucolytic agent, decongestant, dopamine agonist, medicament for gastrointestinal tract, muscle relaxant agent, neuromuscular blocking agent, parasympathetic agonist, prostaglandin, stimulant, anorectic agent, thyroid agent or antithyroid agent, hormone, antimigraine agent, anti-obesity agent, anti-inflammatory agent and the like.

In a particularly preferable embodiment, the drug that can be introduced into a cell is a nucleic acid. The nucleic acid is not particularly limited, and may be any such as DNA, RNA, chimeric nucleic acid of DNA and RNA, DNA/RNA hybrid and the like. A nucleic acid having any of 1 to 3 chains can be used, with preference given to single strand or double strand. The nucleic acid may be other type of nucleotide such as N-glycoside of purine or pyrimidine base, or other oligomer having a non-nucleotide backbone (e.g., commercially available peptide nucleic acid (PNA) etc.) or other oligomer having a special bond (said oligomer comprising base pairing or a nucleotide having a configuration permitting attachment of base, which are found in DNA and RNA) and the like. Furthermore, it may be a nucleic acid added with known modification, for example, one with a label known in the field, one with a cap, methylated one, one or more natural nucleotides substituted by an analog, one with intramolecular nucleotidyl modification, for example, one with non-charge bond (e.g., methylphosphonate, phosphotriester, phosphoramidate, carbamate and the like), one with a charged bond or sulfur-containing bond (e.g., phosphorothioate, phosphorodithioate and the like), for example, one with a side chain group such as protein (nuclease, nuclease inhibitor, toxin, antibody, signal peptide and the like), sugar (e.g., monosaccharide and the like) and the like, one with an intercalating compound (e.g., acridine, psoralen and the like), one with a chelate compound (e.g., metal, metal with radioactivity, boron, oxidative metal and the like), one containing an alkylating agent, or one with a modified bond (e.g., α anomer-type nucleic acid and the like).

For example, the kind of the DNA can be selected as appropriate according to the object of use, and is not particularly limited. For example, plasmid DNA, cDNA, antisense DNA, chromosomal DNA, PAC, BAC and the like can be mentioned, with preference given to plasmid DNA, cDNA and antisense DNA. A circular DNA such as plasmid DNA and the like can be digested as appropriate with a restriction enzyme and the like, and also used as a linear DNA.

The kind of the RNA can be selected as appropriate according to the object of use, and is not particularly limited. For example, siRNA, miRNA, shRNA, antisense RNA, messenger RNA, single strand RNA genome, double stranded RNA genome, RNA replicon, transfer RNA, ribosomal RNA and the like can be mentioned, with preference given to siRNA, miRNA, shRNA, mRNA, antisense RNA, and RNA replicon.

The size of the nucleic acid is not particularly limited, and a large nucleic acid molecule (for example, size of about $10^7$ kbp) such as a chromosome (artificial chromosome etc.) and the like to a small molecule nucleic acid (for example, size of about 5 bp) can be introduced. In consideration of the efficiency of introduction of a nucleic acid into a cell, it is preferably not more than 15 kbp. For example, the size of a polymeric nucleic acid such as plasmid DNA is 2-15 kbp, preferably 2-10 kbp, more preferably 4-10 kbp can be mentioned. The size of a comparatively low molecule nucleic acid such as siRNA is 5-1000 bp, preferably 10-500 bp, more preferably 15-200 bp can also be mentioned.

The nucleic acid may be naturally occurring or synthesized, and a nucleic acid having a size of about 100 bp or below can be synthesized by the phosphotriethyl method, phosphodiester method and the like, by utilizing an automatic nucleic acid synthesizer generally used.

While the nucleic acid used in the present invention is not particularly limited, it is preferably purified by a method generally used by those of ordinary skill in the art.

The above-mentioned drug may form the complex of the present invention together with the antigen of the present invention. Therefore, the drug delivery complex of the present invention may be a drug delivery complex incorporating an antigen.

When the drug delivery into a cell or organ by the drug delivery complex of the present invention aims at the diagnosis or imaging of a cell or organ, the drug can be a compound subjected to a modification suitable for diagnostic apparatus or imaging apparatus (e.g., nuclide, compound labeled (radiolabeled) with nuclide, fluorescent dye, compound labeled with fluorescent dye and the like) (hereinafter these are sometimes to be generically abbreviated as the "nuclide for imaging").

Examples of such drug include radioactive nuclide for positron-emission tomography (PET) ($^{11}C$, $^{13}N$, $^{15}O$, $^{18}F$ and the like) or compound labeled with said nuclide, radioactive nuclide for single photon emission computed tomography (SPECT) ($^{67}Ga$, $^{99m}Tc$, $^{111}In$, $^{123}I$ and the like) or compound labeled with said nuclide, contrast agent for MRI (nuclear magnetic resonance image diagnosis) ($Gd^{3+}$ and the like) or compound labeled with said contrast agent, dye (isosulfan blue, sulfan blue, methylene blue, indocyanine green, indigo carmine and the like) or compound labeled with said dye, fluorescent dye or compound labeled with said fluorescent dye (lanthanoid forming fluorescent complex and the like), as well as a compound used as a molecule probe or tracer. These compounds can be produced by those of ordinary skill in the art by a method known per se.

Alternatively, these nuclides for imaging can also be bound to the below-mentioned various cationic molecules and anionic molecules (preferably, cationic molecule) by a covalent bond or coordinate bond. Such binding method is known to those of ordinary skill in the art.

The compound to be included as the above-mentioned drug in the drug delivery complex of the present invention is not particularly limited, and nuclide, dye, fluorescent dye, molecular probe, diagnostic reagent and the like known per se are used.

That is, the drug delivery complex of the present invention can be used as a carrier for delivering a nuclide for imaging. Said complex heads towards a particular cell or organ since the drug delivery complex of the present invention is cell- or organ-oriented, and therefore, the object region can be more accurately diagnosed and imaged by using the drug delivery complex of the present invention as a carrier for delivering a nuclide for imaging, as compared to the conventional diagnostic method and imaging method using only a nuclide for imaging.

Alternatively, the drug delivery complex of the present invention itself can be used as a molecular probe for a drug used as a diagnostic or imaging reagent.

The drug delivery complex of the present invention does not cause red blood cell agglutination, has low cytotoxicity, is superior in the cellular uptake efficiency, and is cell- or organ-oriented, and therefore, it is a molecular probe that can be used safely and effectively.

When the drug delivery complex of the present invention is used as a carrier for delivering a nuclide for imaging, the drug of the present invention is preferably produced as a complex of a cationic dendrimer and a chelating agent (hereinafter sometimes to be abbreviated as a drug complex).

A drug such as a dye or fluorescent dye molecule and the like can be introduced into a cationic group (e.g., amino group) of a cationic dendrimer via a covalent bond, and a drug such as radioactive nuclide, MRI contrast agent, lanthanoid and the like can also be introduced into a chelating agent.

A method of binding a chelating agent to a cationic dendrimer, and a production method of a complex of the drug of the present invention and a cationic dendrimer and a chelating agent are known to those of ordinary skill in the art. For example, as a production method of a drug complex, a method including mixing a cationic dendrimer and a chelating agent to form a complex of the cationic dendrimer and the chelating agent, and label this with a nuclide for imaging can be mentioned.

By applying a drug produced as a complex of a cationic dendrimer and a chelating agent, the carrier of the present invention can also be applied as a multimodality imaging probe.

When used therefor, a cationic dendrimer to be contained in the drug complex includes a polyamideamine dendrimer and the like. As a chelating agent, p-SCN benzyldiethylenetriamine pentaacetic acid (DTPA) and the like can be mentioned.

The anionic molecule used in the complex of the present invention is a molecule that forms a cell- or tissue-oriented complex together with the aforementioned antigen, the below-mentioned drug, and a cationic molecule, and acts as an anion. The anionic molecule associates with the below-mentioned cationic molecule by an electrostatic interaction and forms the complex of the present invention, which substantially has no electric charge or has negative surface charge.

Examples of preferable anionic molecule include anionic polymer, anionic lipid (e.g., lauroylsarcosine (hereinafter sometimes to be abbreviated as LS), phosphatidylserine (hereinafter sometimes to be abbreviated as DOPS) and the like), gene negatively charged as a whole (e.g., aptamer and the like), antibody negatively charged as a whole and the like. Of these, for example, lauroylsarcosine, γ-polyglutamic acid (hereinafter sometimes to be abbreviated as γ-PGA), glycyrrhizin (hereinafter sometimes to be abbreviated as GLY), phosphatidylserine, chondroitin sulfate, alginic acid and the like are particularly preferable.

These anionic molecules may contain various nuclides (e.g., natural radioactive nuclide, artificial radioactive nuclide, positron-emitting nuclide and the like), or radiolabeled with nuclide. Alternatively, it may be labeled with various compounds (e.g., known fluorescent dye, enzyme and the like).

Each anionic molecule may take the form of a salt, and as the form of a salt, sodium salt, potassium salt, magnesium salt, calcium salt, aluminum salt, hydrochloride and the like can be mentioned.

In the complex of the present invention, the anionic molecule is a most important molecule for obtaining a cell- or organ-oriented complex.

For example, when it is spleen, lung or liver-oriented, the anionic molecule is desirably selected from phosphatidylserine, lauroylsarcosine and glycyrrhizin. Particularly when it is spleen-oriented, phosphatidylserine is desirably selected, when it is lung-oriented, lauroylsarcosine is desirably selected, and when it is liver-oriented, glycyrrhizin is desirably selected.

In each organ, the cell into which the complex of the present invention is incorporated is not particularly limited, and it may be any cell that forms each organ. For example, the complex of the present invention, which is liver-oriented, is incorporated into the hepatic parenchymal cell.

The anionic lipid can also be used as a constituent component of the liposome in the complex of the present invention. As such anionic lipid, phosphatidylserine, phosphatidylinositol, phosphatidic acid, phosphatidylglycerol, LS and the like can be mentioned.

In one embodiment of the present invention, the anionic molecule can be selected from aptamer, miRNA and antibody.

In the present specification, the aptamer is an RNA or DNA-based ligand having high affinity and high specificity, which is produced by an in vitro selection method (SELEX: systematic evolution of ligands by exponential enrichment). Aptamer is produced from a 20-30 nucleotide random sequence, selectively screened for by the adsorption to a molecular antigen or cell, and enriched to specifically purify a high affinity binding ligand. To enhance stability and practicality in vivo, aptamer is generally modified chemically to inhibit nuclease degradation and facilitate binding to a medicament, a label or a particle. In addition, a nucleic acid not specifically involved in the interaction with a ligand is substituted by a simpler chemical crosslinking method. While an aptamer does not have a structure in a solution, it can undergo folding and enclose a target epitope, whereby the epitope is specifically recognized. The specific folding of nucleic acid around the epitope leads to a recognizable intermolecular contact mediated by a hydrogen bond, an electrostatic action, stacking or shape complementarity. When compared to a protein-based ligand, generally, aptamer is stable, shows high conductivity in heating sterilization and has low immunogenicity. Aptamer is currently used for angiogenesis, activated platelet, and many clinically significant lesions including solid tumor as targets, and the use thereof is increasing. When an aptamer is used as a targeting ligand in imaging and/or emulsion particles for treatment, its clinical usefulness may depend on the negative charge intensity of the surface, which is conferred by a phosphate group in a nucleic acid, relative to the clearance rate. Previous studies using lipid-based particles show that negative zeta potential markedly decreases liposomal half-life in blood, whereas neutral or cationic particles are commonly sustained systemically for a longer time.

The aptamer of the present invention may take the form of a salt. As such aptamer salt, sodium salt, potassium salt, magnesium salt, calcium salt, aluminum salt and the like can be mentioned. The aptamer or a salt thereof used may be commercially available (e.g., manufactured by Hokkaido System Science), or can be produced as appropriate by using the conventional protocol.

In the complex of the present invention, as an antibody when used as an anionic molecule is not particularly limited as long as it acts as an anionic molecule (e.g., an antibody whose whole antibody surface is negatively charged). Using an antibody as an anionic molecule enables the complex to be more cell- or organ-oriented utilizing an antigen antibody reaction. The antibody used may be commercially available, or can also be produced as appropriate against a selected antigen, by using the conventional protocol.

In one embodiment of the present invention, the anionic molecule used in the complex of the present invention is selected from γ-polyglutamic acid, chondroitin sulfate (hereinafter sometimes to be abbreviated as CS), alginic acid (hereinafter sometimes to be abbreviated as AGA) and a salt thereof. The anionic molecule in this embodiment is preferably γ-PGA.

In the present specification, as γ-PGA or a salt thereof, a compound represented by the following formula (1) can be mentioned.

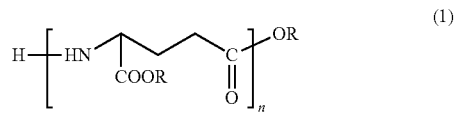

wherein R is a hydrogen atom, an alkali metal atom such as sodium, potassium, lithium and the like, a tertiary amine such as trimethylamine, triethylamine, dimethylamine, diethylamine, triethanolamine, trimethanolamine, diethanolamine, dimethanolamine, ethanolamine and the like, or a quaternary amine such as tetramethylamine, tetraethylamine and the like, each R in a molecule may be the same or different, and n is an integer of not less than 40.

In the present specification, as CS or a salt thereof, a compound represented by the following formula (2) can be mentioned.

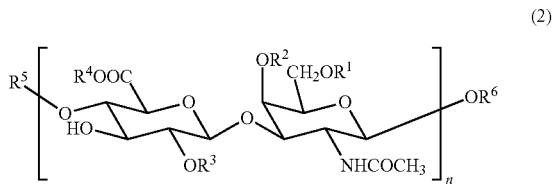

wherein $R^1$-$R^3$ are each independently a hydrogen atom or a sulfonate group (wherein at least one of $R^1$ and $R^2$ is a sulfonate group), $R^4$-$R^6$ are each independently a hydrogen atom, an alkali metal atom such as sodium, potassium, lithium and the like, a tertiary amine such as trimethylamine, triethylamine, dimethylamine, diethylamine, triethanolamine, trimethanolamine, diethanolamine, dimethanolamine, ethanolamine and the like, or a quaternary amine such as tetramethylamine, tetraethylamine and the like, each sulfonate group in a molecule may be substituted by an alkali metal atom such as sodium, potassium, lithium and the like, a tertiary amine such as trimethylamine, triethylamine, dimethylamine, diethylamine, triethanolamine, trimethanolamine, diethanolamine, dimethanolamine, ethanolamine and the like, or a quaternary amine such as tetramethylamine, tetraethylamine and the like, and n is an integer of not less than 10.

In the present specification, as AGA or a salt thereof, a compound represented by the following formula (3) can be mentioned.

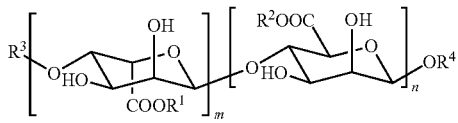

wherein $R^1$-$R^4$ are each independently a hydrogen atom, alkali metal atom such as sodium, potassium, lithium and the like, a tertiary amine such as trimethylamine, triethylamine, dimethylamine, diethylamine, triethanolamine, trimethanolamine, diethanolamine, dimethanolamine, ethanolamine and the like, or a quaternary amine such as tetramethylamine, tetraethylamine and the like, m and n shows the total number of respective blocks in the block copolymer, and the total of m and n is not less than 20.

In the present specification, LS is a compound represented by the following formula (4).

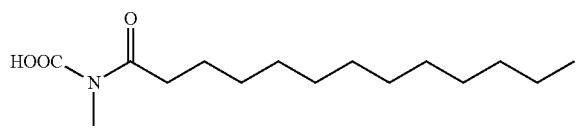

As the salt of LS, sodium salt, potassium salt, magnesium salt, calcium salt, aluminum salt and the like can be mentioned.

In the present specification, phosphatidylserine is a compound represented by the following formula (5).

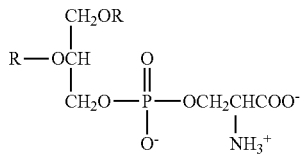

As the salt of phosphatidylserine, sodium salt, potassium salt, magnesium salt, calcium salt, hydrochloride and the like can be mentioned.

In the present specification, glycyrrhizin is a compound represented by the following formula (6).

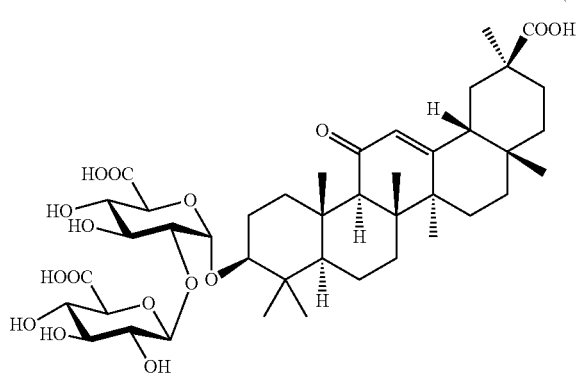

As the salt of glycyrrhizin, sodium salt, potassium salt, magnesium salt, calcium salt, hydrochloride and the like can be mentioned.

These anionic molecules can be each prepared by a method known per se.

When the anionic molecule is a polymer, i.e., γ-PGA, CS, AGA or a salt thereof, its degree of polymerization is not particularly limited. For example, one having a molecular weight of not less than 5,000, more preferably not less than 10,000, can be mentioned. In addition, the anionic polymer has a molecular weight of, for example, not more than 200,000, preferably not more than 150,000, more preferably not more than 100,000, so that it can encapsulate an antigen stably without an influence of the amount of the anionic molecule contained.

When antigen or drug delivery into a cell or organ by the drug delivery complex of the present invention aims at the diagnosis or molecule imaging of a cell or organ, the anionic molecule can be an anionic molecule modified by a nuclide for imaging, which is suitable for a diagnostic apparatus (method) or an imaging apparatus (method).

Examples of such anionic molecule include radioactive) nuclides for positron-emission tomography (PET) ($^{11}$C, $^{13}$N, $^{15}$O, $^{18}$F and the like) or an anionic molecule labeled with said nuclide, radioactive nuclide for single photon emission computed tomography (SPECT) ($^{67}$Ga, $^{99m}$Tc, $^{111}$In $^{123}$I and the like) or an anionic molecule labeled with said nuclide, contrast agent for MRI (nuclear magnetic resonance image diagnosis) ($Gd^{3+}$ and the like) or an anionic molecule labeled with said contrast agent, dye (isosulfan blue, sulfan blue, methylene blue, indocyanine green, indigo carmine and the like) or an anionic molecule labeled with said dye, fluorescent dye or an anionic molecule labeled with said fluorescent dye. These anionic molecules can be produced by those of ordinary skill in the art by a method known per se.

For example, various signal metals (radioactive nuclide, magnetic metal, lanthanoid forming a fluorescent complex and the like) used for PET, SPECT, MRI and the like can be introduced into an anionic molecule by forming a coordinate bond with a chelating agent, and various dyes can be introduced by forming a covalent bond with an anionic molecule. The introduction methods thereof are known to those of ordinary skill in the art.

The cationic molecule used in the complex of the present invention may be any as long as it can form a complex with the above-mentioned anionic molecule by an electrostatic interaction. Examples thereof include, but are not limited to, cationic polymers [for example, polyethylenimine (hereinafter sometimes to be abbreviated as PEI), polycationic polysaccharide such as chitin and chitosan, polycationic polypeptide such as polylysine, polyarginine, protamine and the like], or cationic lipid [lipid such as, for example, phospholipid such as phosphatidylcholine (soybean phosphatidylcholine, egg-yolk phosphatidylcholine, distearoylphosphatidylcholine, dipalmitoylphosphatidylcholine etc.), phosphatidylethanolamine (distearoylphosphatidylethanolamine etc.), phosphatidylserine, phosphatidic acid, phosphatidylglycerol, phosphatidylinositol, lysophosphatidylcholine, sphingomyelin, egg-yolk lecithin, soybean lecithin, hydrogenated phospholipid, for example, glycerolglycolipid such as sulfoxyribosyl glyceride, diglycosyl diglyceride, gigalactosyl diglyceride, galactosyl diglyceride, glycosyl diglyceride, for example, sphingoglycolipid such as galactosyl cerebroside, lactosyl cerebroside, ganglioside, which undergoes introduction with amino group, alkylamino group, dialkylamino group, trialkylammonium group, monoacyloxyalkyl-dialkylammonium group, diacyloxyalkyl-monoalkylammonium group, quaternary ammonium group such as diacyloxyalkyl-trialkylammonium group, N-[1-(2,3-dioleyloxy)propyl]-N,N,N-trimethylammonium chloride (hereinafter sometimes to be abbreviated as DOTMA), N-[1-(2,3-Dioleoyloxy)propyl]-N,N,N-trimethylammonium methyl-sulfate (hereinafter sometimes to be abbreviated as DOTAP), 3beta-[N—(N',N'-dimethylaminoethane)carbamoyl]cholesterol (hereinafter sometimes to be abbreviated as DC-Chol), benzalkonium chloride], cationic surfactant [for example, benzalkonium chloride, benzethonium chloride and the like], cationic dendrimer [for example, polyamideamine dendrimer and the like] and the like.

These cationic molecules can be respectively prepared by a method known per se.

Preferable examples of the cationic molecule of the present invention include a cationic polymer selected from polylysine, polyarginine, polyhistidine, polyethylenimine and cationic dendrimer, a cationic lipid selected from DOTMA, DOTAP, DC-Chol and benzalkonium chloride, and benzalkonium chloride.

These cationic molecules may contain various nuclides (e.g., natural radioactive nuclide, artificial radioactive nuclide, positron-emitting nuclide and the like), or radiolabeled with nuclide. Alternatively, it may be labeled with various compounds (e.g., known fluorescent dye, enzyme and the like).

When antigen or drug delivery into a cell or organ by the drug delivery complex of the present invention aims at the diagnosis or molecule imaging of a cell or organ, the cationic molecule can be a cationic molecule modified by a nuclide for imaging, which is suitable for a diagnostic apparatus (method) or an imaging apparatus (method).

Examples of such cationic molecule include radioactive) nuclides for positron-emission tomography (PET) ($^{11}$C, $^{13}$N, $^{15}$O, $^{18}$F and the like) or an cationic molecule labeled with said nuclide, radioactive nuclide for single photon emission computed tomography (SPECT) ($^{67}$Ga, $^{99m}$Tc, $^{111}$In, $^{123}$I and the like) or a cationic molecule labeled with said nuclide, contrast agent for MRI (nuclear magnetic resonance image diagnosis) ($Gd^{3+}$ and the like) or a cationic molecule labeled with said contrast agent, dye (isosulfan blue, sulfan blue, methylene blue, indocyanine green, indigo carmine and the like) or a cationic molecule labeled with said dye, fluorescent dye or a cationic molecule labeled with said fluorescent dye. These cationic molecules can be produced by those of ordinary skill in the art by a method known per se.

For example, various signal metals (radioactive nuclide, magnetic metal, lanthanoid forming a fluorescent complex and the like) used for PET, SPECT, MRI and the like can be introduced into a cationic molecule by forming a coordinate bond with a chelating agent, and various dyes can be introduced by forming a covalent bond with an anionic molecule. The introduction methods thereof are known to those of ordinary skill in the art.

The complex of an antigen or drug and a cationic molecule (hereinafter sometimes to be referred to as a cationic complex) constituting the complex of the present invention may take any form as long as the cationic complex can form an antigen delivery complex which is substantially not electrically charged or has a negative surface charge, by an electrostatic interaction with an anionic molecule. Examples thereof include, but are not limited to,
(a) a positive surface charged complex obtained by self-assembly by mixing an antigen or drug and a cationic molecule (including liposome or micell constituted with a cationic polymer or cationic lipid) (hereinafter sometimes to be referred to as a self-assembled complex);
(b) a cationic micelle encapsulating an antigen or drug (microsphere);
(c) a cationic liposome encapsulating an antigen or drug;
(d) a positively surface-charged complex obtained by self-assembly by mixing a drug that forms a complex of a cationic dendrimer and a chelating agent, and a cationic molecule and the like. The liposome may be any of a single layer type and a multilayer type.

Particularly, when the drug is siRNA in the drug delivery complex of the present invention, the complex of the present invention is preferably self-assembled with a liposome comprising dioleyl phosphatidylethanolamine.

Those of ordinary skill in the art can appropriately select the form of the cationic complex according to the physicochemical properties of the antigen or drug to be contained. In the case of a water-soluble antigen or drug having a negative charge such as DNA, inactivated virus and the like, the complex of the above-mentioned (a) or (c) can be used. In the case of a positively charged, water-soluble antigen or drug, the complex of the above-mentioned (c) can be used. Alternatively, when a drug is handled as a drug complex with a cationic dendrimer and a chelating agent, the complex of the above-mentioned (d) can be used.

When a cancer antigen is used as an antigen or drug, which is another embodiment of the present invention, the above-mentioned cationic complex preferably takes the form of a micell.

The cationic complex may have a combined form of two or more of the above-mentioned forms, as long as it has a positive surface charge. Examples thereof include, but are not limited to, the form of a cationic liposome including a complex of the above-mentioned (a) or (b), and any other optional combination can be employed.

Specific examples of such form include a cationic complex constituted with an antigen or drug, and a cationic polymer and/or a cationic lipid. In this embodiment, the cationic polymer is selected from polylysine, polyarginine, polyhistidine, polyethylenimine and cationic dendrimer, and the cationic lipid is preferably selected from DOTMA, DOTAP, DC-Chol and benzalkonium chloride.

Other specific examples include a cationic complex constituted with an antigen or drug, and a cationic polymer and/or a cationic lipid. In this embodiment, the cationic polymer is selected from polylysine, polyarginine, polyhistidine, polyethylenimine and cationic dendrimer, and the cationic lipid is particularly preferably selected from DOTMA, DOTAP, DC-Chol and benzalkonium chloride.

In addition, micell and liposome may contain, besides the cationic lipid molecule, a neutral lipid (phospholipid, peptidelipid, glycolipid and the like; for example, dioleyl phosphatidylethanolamine (hereinafter sometimes to be abbreviated as DOPE), cholesterol and the like), polyoxyalkyleneglycol (PEG, PPG etc.) and the like known per se as a component molecule.

As a cationic complex in such form, a cationic complex constituted with a liposome or micell consisting of an antigen or drug, a cationic lipid and a lipid selected from DOPE and cholesterol can be mentioned. In this embodiment, the cationic lipid is particularly preferably selected from DOTMA, DOTAP and DC-Chol.

While the mixing ratio of the antigen or drug and the cationic molecule used for the preparation of the cationic complex of the present invention is not particularly limited, for example, when the cationic complex is a self-assembled complex obtained by mixing a negatively charged antigen or drug and a cationic molecule, the molar ratio of the negatively charged functional group of the antigen (e.g., phosphate group in DNA, carboxyl group in protein and peptide, etc.), and the positively charged functional group of the cationic molecule (e.g., imino group in PEI, amino group in polylysine and polyarginine etc.) is 1:1-1:20, preferably 1:2-1:15, more preferably 1:2-1:10, when used.

In the present specification, the "mixing ratio" means the ratio of the following values in the substance that forms the complex of the present invention.

antigen or drug: the number of moles of the functional group having a negative charge cationic molecule (cationic polymer and cationic lipid): the number of moles of the functional group having a positive charge neutral lipid: the number of moles anionic molecule: the number of moles of the functional group having a negative charge That is, the "mixing ratio" can also be defined by the "charge ratio" of the cationic functional group (for example, amino group) or anionic functional group (for example, carboxyl group and sulfonyl group) in each substance that forms the complex of the present invention.

When the cationic complex of the present invention takes the form of a liposome by the addition of a cationic lipid, the molar ratio of the negatively charged functional group of the antigen or drug (e.g., phosphate group in DNA, carboxyl group in protein and peptide, etc.), and the positively charged functional group of the cationic molecule (e.g., quaternary ammonium group in diacyloxyalkyl-trialkylammonium group and the like) is 1:1:1-1:20:20, preferably 1:2:2-1:15:15, more preferably 1:2:2-1:10:10, when used, which is appropriately set within the range where the form of a liposome is maintained.

When the cationic complex of the present invention takes the form of a liposome by the addition of a neutral lipid known per se, a neutral lipid only needs to be mixed with an antigen or drug and a cationic molecule, where the mixing ratio can be appropriately determined by those of ordinary skill in the art.

Such cationic complex of the present invention can be prepared by appropriately mixing an antigen and a cationic molecule. The technique and experiment apparatuses necessary for the preparation, and various conditions of reaction time, reaction temperature and the like can be appropriately set by those of ordinary skill in the art.

In the complex of the present invention, the above-mentioned cationic complex is encapsulated in the above-mentioned anionic molecule. The "encapsulated" here means that it is contained inside. For example, it may be a non-inclusive form where the surface of the cationic complex is covered with anionic molecules bound by an electrostatical interaction, or a form of inclusion of a cationic complex like a liposome. In the former case, as long as the complex has substantially no electric charge or negative surface charge, the cationic complex does not need to be completely coated with an anionic molecule. The complex has "substantially no electric charge" means when the complex is contacted with the blood, red blood cell agglutination does not occur, and the positive charge is low to the level that the survival rate of the cell upon contact of the complex with the cell is at least 50%. Specifically, the surface charge ($\zeta$ potential) of the complex is not more than +20 mV, preferably not more than +10 mV, more preferably not more than +5 mV, still more preferably not more than 0 mV, further preferably not more than −10 mV, particularly preferably not more than −15 mV. While the lower limit of the surface charge ($\zeta$ potential) is not particularly limited, it is, for example, not less than −50 mV, preferably not less than −40 mV, more preferably not less than −30 mV.

While the mixing ratio of the cationic molecule and the anionic molecule used for the preparation of the complex of the present invention is not particularly limited as long as the complex has substantially no electric charge or negative surface charge. The molar ratio of the positively charged functional group of the cationic molecule (e.g., imino group in PEI, amino group in polylysine and polyarginine, etc.), and the negatively charged functional group of the anionic molecule (e.g., sulfonate group and carboxyl group in γ-PGA, AGA, CS) is 5:1-1:5, preferably 4:1-1:4, more preferably 3:1-1:4. However, the ratio is not limited, since it can be optimized according to the properties of the cationic molecule.

When the cationic complex of the present invention takes the form of a liposome by the addition of a cationic lipid, the molar ratio of the cationic molecule and the anionic molecule is such that the molar ratio of positively charged functional group of the cationic molecule (e.g., imino group in PEI, amino group in polylysine and polyarginine, etc.), the positively charged functional group of the cationic lipid (e.g., quaternary ammonium group in diacyloxyalkyl-trialkylammonium group and the like), and the negatively charged functional group of anionic molecule (e.g., LS, phosphatidylserine, phosphate group and carboxyl group of aptamer) is 1:1:1-1:1:5, preferably 1:1:1-1:1:4, more preferably 1:1:1-1:1:2, when used, which is appropriately set within the range where the form of a liposome is maintained.

The above-mentioned mixing ratio is important for the complex of the present invention to be desirably cell- or organ-oriented.

In one embodiment of the present invention, when the anionic molecule is phosphatidylserine, the obtained complex of the present invention is spleen-oriented, as mentioned above. In this case, however, adjusting the mixing ratio of an antigen or drug, a cationic molecule, and an anionic molecule phosphatidylserine to 1:2:4-1:8:8 enables the complex to be more spleen-oriented.

That is, in a preferable embodiment of the present invention, a spleen-oriented complex is provided wherein the anionic molecule is phosphatidylserine; and the mixing ratio of an antigen or drug, a cationic molecule, and phosphatidylserine is 1:2:4-1:8:8. With the mixing ratio within this range, the complex of the present invention having a surface electric charge, which is optimally oriented to the spleen, can be obtained.

While the cationic polymer and cationic lipid in this case are not particularly limited, they are preferable polyethylenimine, polylysine, polyarginine.

In one embodiment of the present invention, when the anionic molecule is lauroylsarcosine, the obtained complex of the present invention is lung-oriented, as mentioned above. In this case, however, when the cationic molecule is a cationic polymer and cationic lipid, adjusting the mixing ratio of an antigen or drug, a cationic polymer, a cationic lipid and an anionic molecule lauroylsarcosine to 1:2:2:1-1:2:2:4 enables the complex to be more lung-oriented. That is, in a preferable embodiment of the present invention, a lung-oriented complex is provided wherein the anionic molecule is lauroylsarcosine; the cationic molecule consists of a cationic polymer and a cationic lipid; and the mixing ratio of an antigen or drug, a cationic molecule, and phosphatidylserine is 1:2:2:1-1:2:2:4. With the mixing ratio within this range, the complex of the present invention having a surface electric charge, which is optimally oriented to the lung can be obtained.

While the cationic polymer and cationic lipid in this case are not particularly limited, the cationic polymer is preferably polyethylenimine, polylysine or polyarginine, and the cationic lipid is preferably DOTMA or DOTAP.

In one embodiment of the present invention, when the anionic molecule is glycyrrhizin, the obtained complex of the present invention is liver-oriented, as mentioned above. In this case, however, adjusting the mixing ratio of an antigen or drug, a cationic molecule, and an anionic molecule glycyrrhizin to 1:2:8-1:8:16 enables the complex to be more liver-oriented.

That is, in a preferable embodiment of the present invention, a liver-oriented complex is provided wherein the anionic molecule is glycyrrhizin; and the mixing ratio of an antigen or drug, a cationic molecule, and glycyrrhizin is 1:2:8-1:8:16. With the mixing ratio within this range, the complex of the present invention having a surface electric charge, which is optimally oriented to the liver, can be obtained.

The antigen or drug in this case is preferably a nucleic acid. The cationic molecule is preferably polyethylenimine, polylysine or polyarginine.

In another embodiment of the present invention, when the anionic molecule is γ-polyglutamic acid, the obtained complex of the present invention is dendritic cell- or spleen-oriented, as mentioned above.

Particularly, when a protein antigen is used as an antigen or drug, renders the complex still more dendritic cell-oriented using benzalkonium chloride as a cationic molecule and γ-polyglutamic acid as an anionic molecule.

The complex of the present invention can be prepared by contacting an antigen or drug with a cationic molecule at a suitable mixing ratio to form a cationic complex, and further contacting the cationic complex with an anionic molecule at a suitable mixing ratio.

For example, a cationic complex utilizing an electrostatic interaction between a water-soluble antigen or drug having a negative charge such as DNA and the like and a water-soluble cationic polymer such as PEI and the like can be prepared by mixing an antigen or drug with a cationic polymer in water or a suitable buffer, and incubating the mixture at room temperature for 0.5-300 min, preferably 1-180 min. The concentration of the antigen or drug in the mixture can be appropriately set in consideration of the kind, size (molecular weight) and the like of the antigen or drug to be used. When the antigen or drug is a DNA, it is generally within the range of 0.01-1000 ng/μL. When the antigen or drug is general plasmid DNA (size of about 4-7 kbp), the DNA concentration of said mixture is preferably within the range of 50-500 ng/μL. When the concentration is too low, the DNA introduced into the cell cannot express the expected function, and when the concentration is too high, the nucleic acid introduction efficiency reduces. The mixing ratio of the antigen or drug and the cationic polymer can be appropriately selected from the above-mentioned range. The incubation time of the mixture can be appropriately selected within the above-mentioned range according to the kind of the antigen or drug and the cationic polymer to be used. When the incubation time is too short, formation of a complex of the antigen or drug and the cationic polymer becomes insufficient, and when the incubation time is too long, the formed complex sometimes becomes unstable. In both cases, the delivery efficiency of the antigen or drug to the cell becomes low.

In the case of a cationic micell encapsulating an antigen or drug, for example, a cationic lipid salt and a lipophilic antigen or drug are dissolved in chloroform, sufficiently blended, and chloroform is completely removed by an evaporator and a desiccator. Any isotonic solution is added and the mixture is hydrated overnight. After hydration, a cationic micell encapsulating the antigen or drug is prepared by sonication. The amount of the antigen or drug used for the preparation and the mixing ratio with the cationic lipid can be appropriately adjusted by the physicochemical properties such as lipophilicity and the like of the antigen or drug. Other than this method, a micell can be prepared by a known method. The amount of the antigen or drug to be used, and the mixing ratio of the antigen or drug and the cationic lipid can be respectively selected as appropriate from the above-mentioned ranges.

A cationic liposome encapsulating an antigen or drug can be prepared by a method known per se, for example, sonication, heating, vortex, ether injection method, French press method, cholic acid method, $Ca^{2+}$ fusion method, freeze-thaw method, reverse phase evaporation method and the like. The amount of the antigen or drug to be used, and the mixing ratio of the antigen or drug and the cationic lipid can be respectively selected as appropriate from the above-mentioned ranges.

An anionic molecule is added to the obtained cationic complex solution and the mixture is incubated at room temperature for 0.5-300 min, preferably 15-60 min, to allow self-assembly, whereby antigen delivery complex wherein the cationic complex is coated with the anionic molecule can be obtained. When the incubation time is too short, formation of a complex of the cationic complex and the anionic molecule becomes insufficient, and when the incubation time is too long, the formed complex sometimes becomes unstable. In both cases, the delivery efficiency of the antigen to the cell becomes low. The mixing ratio of the cationic molecule constituting the cationic complex and the anionic molecule can be selected as appropriate from the above-mentioned range.

The thus-obtained complex of the present invention has a surface with substantially no electric charge or negative charge. The "substantially no electric charge" here is as mentioned above. Specifically, substantially no electric charge means that the surface charge (ζ potential) is not more than +20 mV and not less than −20 mV, preferably not more than +10 mV and not less than −10 mV, more preferably not more than +5 mV and not less than −5 mV. In addition, the "negative surface charge" means not more than 0 mV, preferably not more than −5 mV, more preferably not more than −10 mV, still more preferably not more than −15 mV. While the lower limit of the surface charge (ζ potential) is not particularly set, for example, it is not less than −50 mV, preferably not less than −40 mV, more preferably not less than −30 mV. The ζ potential of the antigen or drug delivery complex can be measured using a commercially available ζ potential measuring apparatus.

Since the complex of the present invention has substantially no electric charge or negative electric charge, agglutination of red blood cell does not occur even by systemic administration such as intravenous administration and the like, unlike conventional carrier molecules using cationic polymers such as PEI and the like and a cationic liposome. In addition, non-specific antigen delivery to a cell other than the target is also reduced.

The complex of the present invention has an average particle size of not more than 500 nm, preferably not more than 300 nm, more preferably not more than 200 nm. The particle size distribution and average particle size of the complex can be calculated, for example, from the scattering intensity distribution obtained using a dynamic light scattering measuring apparatus.

Conventionally, an attempt has been made to enhance migration into an organ such as lung and the like by causing embolism in the reticuloendothelial system of the target site by increasing the particles size. However, this technique is associated with a risk of causing embolism since the particles may be lodged in the capillary of the system. In contrast, since the complex of the present invention having a particle size almost equivalent to that of the cationic complex achieves sufficient retention, and can improve delivery efficiency of an antigen or drug to a particular organ, it enables safe systemic administration.

Since the complex of the present invention remarkably reduces cytotoxicity as compared to a cationic complex free of an anionic molecule and using a cationic polymer such as PEI and the like, it can minimize undesirable side effects.

The complex of the present invention can be used alone, or formulated according to a conventional means together with a pharmacologically acceptable carrier, and used as a medicament or reagent composition. When the complex is formulated as a reagent composition, the complex can be provide as it is or as a sterile solution or suspension with, for example, water or other physiologically acceptable solution (e.g., aqueous solvent such as saline, phosphate-buffered saline (PBS), medium used for conventional cell culture (for example, RPMI1640, DMEM, HAM F-12, Eagle medium etc.) and the like, organic solvent such as ethanol, methanol, DMSO and the like or a mixture of aqueous solvent and organic solvent etc.). The composition can appropriately contain physiologically acceptable excipient, vehicle, preservative, stabilizer, binder and the like known per se.

When the complex of the present invention is formulated as a pharmaceutical composition, the complex can be provide as it is or as an oral preparation (for example, tablet, capsule etc.) or parenteral agent (for example, injection, spray etc.) by blending the complex with a pharmaceutically acceptable carrier, flavor, excipient, vehicle, preservative, stabilizer, binder and the like in a conventionally admitted unit dosage form required for practicing preparation formulation.

Examples of the additive that can be blended into tablet, capsule and the like include binders such as gelatin, cornstarch, tragacanth, gum arabic, excipients such as crystalline cellulose, swelling agents such as corn starch, gelatin and the like, lubricants such as magnesium stearate, sweetening agents such as sucrose, lactose or saccharin, flavor such as peppermint, *Gaultheria adenothrix* oil or cherry, and the like. When the formulation unit form is capsule, a liquid carrier such as fats and oils can be further added to the above-mentioned types of materials. Examples of the aqueous solution for injection include isotonic solution containing saline, glucose and other auxiliary agents (e.g., D-sorbitol, D-mannitol, sodium chloride and the like) and the like, which may be used in combination with a suitable solubilizing agent, for example, alcohol (e.g., ethanol), poly alcohol (e.g., propylene glycol, polyethylene glycol), non-ionic surfactant (e.g., polysorbate80™, HCO-50) and the like. Examples of the oily liquid include sesame oil, soybean oil and the like, which may be used in combination with a solubilizing agents such as benzyl benzoate, benzyl alcohol and the like.

In addition, the above-mentioned pharmaceutical composition may be blended with, for example, a buffering agent (e.g., phosphate buffer, sodium acetate buffer and the like), a soothing agent (e.g., benzalkonium chloride, procaine hydrochloride and the like), a stabilizer (e.g., human serum albumin, polyethylene glycol and the like), a preservative (e.g., benzyl alcohol, phenol and the like), an antioxidant (for example, ascorbic acid and the like) and the like.

The present invention also provides a delivery method of an antigen or drug into a cell, comprising contacting the above-mentioned complex of the present invention with the cell.

While the kind of the cell is not particularly limited, a prokaryotic or eucaryotic cell can be used, with preference given to a eucaryotic cell. the kind of the eukaryotic cell is not particularly limited and, for example, vertebrates such as mammals including human (human, monkey, mouse, rat, hamster, bovine etc.), birds (chicken, ostrich etc.), amphibia (frog etc.), fishes (zebrafish, rice-fish etc.) and the like, invertebrates such as insects (silk moth, moth, *Drosophila* etc.) and the like, plants, microorganisms such as yeasts and the like, and the like can be mentioned. More preferably, the target cell in the present invention is an animal or plant cell, more preferably a mammalian cell. The cell may be a culture cell line including a cancer cell, or a cell isolated from an individual or tissue, or a cell of a tissue or tissue piece. The cell may be an adherent cell or a non-adherent cell.

A more specific explanation of the step of contacting the complex of the present invention with the cell is, for example, as follows.

That is, the cell is suspended in a suitable medium several days before contact with the complex of the present invention, and cultured under appropriate conditions. At the time of contact with the complex, the cell may or may not be in a growth stage. The culture medium on contact may be a serum-containing medium or a serum-free medium, wherein the serum concentration of the medium is not more than 30%, preferably not more than 20%, since when the medium contains excess protein such as serum and the like, the contact between the complex and the cell may be inhibited.

The cell density on contact is not particularly limited, and can be appropriately determined in consideration of the kind of the cell and the like. It is generally $0.1 \times 10^5 - 5 \times 10^5$ cells/mL, preferably $0.1 \times 10^5 - 4 \times 10^5$ cells/mL, more preferably $0.1 \times 10^5 - 3 \times 10^5$ cells/mL, still more preferably $0.2 \times 10^5 - 3 \times 10^5$ cells/mL, most preferably $0.2 \times 10^5 - 2 \times 10^5$ cells/mL.

A solution containing the complex is added to the thus-prepared medium containing the cells. The amount of the complex-containing solution to be added is not particularly limited, and can be appropriately determined in consideration of the cell number and the like. It is generally 1-1000 µL, preferably 1-500 µL, more preferably 1-300 µL, still more preferably 1-200 µL, most preferably 1-100 µL, per 1 mL of the medium.

The temperature, humidity and $CO_2$ concentration when the complex-containing solution is added to the medium and the cells are cultured can be appropriately determined in consideration of the kind of the cell. In the case of a mammalian cell, temperature about 37° C., humidity about 95% and $CO_2$ concentration about 5% are generally employed.

While the culture time can also be appropriately determined in consideration of the conditions such as the kind of the cell and the like, it is generally 1-72 hr, preferably 1-60 hr, more preferably 1-48 hr, still more preferably 1-40 hr, most preferably 1-32 hr.

When the above-mentioned culture time is too short, the antigen or drug is not sufficiently introduced into the cell, and when the culture time is too long, the cell may become weak.

By the above-mentioned culture, the antigen or drug is introduced into a cell. The culture is further continued preferably by exchanging the medium with a fresh medium, or adding a fresh medium to the medium. When the cell is a mammal-derived cell, the fresh medium preferably contains a serum or nutrition factor.

The time of further culture can be appropriately determined in consideration of the function and the like expected of the antigen or drug. When the antigen or drug is a plasmid DNA such as an expression vector and the like, it is generally 8-72 hr, preferably 8-60 hr, more preferably 8-48 hr, still more preferably 8-36 hr, most preferably 12-32 hr.

The present invention also provides a delivery method of an antigen or drug to a cell or organ of an animal, comprising administering the above-mentioned complex of the present invention to the target.

That is, by administration of the complex of the present invention to a target, the complex reaches or contacts with the target cell or target organ, and the antigen or drug contained in the complex is introduced into the cell or organ in vivo.

The target to which the complex of the present invention can be administered is not particularly limited and, for example, vertebrates such as mammals including human (human, monkey, mouse, rat, hamster, bovine etc.), birds (chicken, ostrich etc.), amphibia (frog etc.), fishes (zebrafish, rice-fish etc.) and the like, invertebrates such as insects (silk moth, moth, *Drosophila* etc.) and the like, plants and the like can be mentioned. The subject of administration of the complex is preferably human or other mammal.

The administration method of the complex of the present invention is not particularly limited as long as the complex reaches or contacts with the target cell or target organ, and the antigen or drug contained in the complex is introduced into the cell or organ, and an administration method known per se (oral administration, parenteral administration (intravenous administration, intramuscular administration, topical administration, transdermal administration, subcutaneous administration, intraperitoneal administration, spray etc.) etc.) can be appropriately selected in consideration of the kind of the antigen or drug, the kind and the site of the target cell or target organ and the like.

The dose of the complex of the present invention is not particularly limited as long as the introduction of an antigen or drug into a cell or organ can be achieved, and can be appropriately selected in consideration of the kind of the subject of administration, administration method, the kind of the antigen or drug, the kind and the site of the target cell or target organ and the like. In the case of oral administration, for example, a single dose thereof as a complex is generally about 0.001 mg-10000 mg for human (body weight 60 kg). In the case of parenteral administration (for example, intravenous administration etc.), for example, a single dose thereof as a complex is generally about 0.0001 mg-3000 mg for human (body weight 60 kg).

When γ-PGA, CS or AGA or a salt thereof, preferably γ-PGA or CS or a salt thereof, more preferably γ-PGA or a salt thereof, is used as an anionic molecule, the complex of the present invention is delivered to the spleen with high selectivity after systemic administration such as intravenous administration and the like.

The present invention also relates to a vaccine containing the complex of the present invention.

Specifically, when a pathogen antigen or a DNA encoding same is used as an antigen or drug, the complex can be used as an infection vaccine, when a cancer antigen is used as an antigen or drug, the complex can be used as a cancer vaccine (hereinafter the infection vaccine and cancer vaccine of the present invention are also generically referred to as the vaccine of the present invention).

As the complex of the present invention to be contained in vaccine of the present invention, those similar to the aforementioned can be used.

The vaccine of the present invention may be the complex per se of the present invention, or formulated together with the above-mentioned pharmaceutically acceptable carrier etc. according to the method generally employed in the field.

The vaccine of the present invention also has an average particle size of not more than 500 nm, preferably not more than 300 nm, more preferably not more than 200 nm, in view of the risk of embolism and the like, as in the case of the complex of the present invention.

The vaccine of the present invention may contain the above-mentioned physiologically acceptable liquid, pharmaceutically acceptable carrier, flavor, excipient, vehicle, preservative, stabilizer, binder and the like.

The vaccine of the present invention also delivers an antigen into a cell by contact with the cell in the same manner as with the complex of the present invention, and can enhance the immunity.

Moreover, the vaccine of the present invention delivers an antigen into a cell by administration thereof to a mammal in the same manner as with the complex of the present invention, and can enhance the immunity.

Alternatively, the present invention relates to a drug delivery complex, which is used as a carrier for the delivery of a nuclide for imaging.

Since the complex of the present invention is delivered to a particular cell or organ as it is oriented to said cell or organ, the above-mentioned carrier (hereinafter sometimes to be described as the carrier of the present invention) can more accurately diagnose the object site than the conventional diagnosis and imaging methods using a probe alone.

The carrier of the present invention may be the complex per se of the present invention or may contain the complex of the present invention.

As mentioned above, when the complex of the present invention is applied to a carrier for a nuclide for imaging (hereinafter sometimes to be described as the imaging probe), the drug of the present invention is preferably produced as a drug complex. The cationic group (e.g., amino group) of a cationic dendrimer can undergo introduction with a drug such as dye, fluorescent dye molecule and the like via a covalent bond, and the chelating agent can also undergo introduction with a drug such as radioactive nuclide, MRI contrast agent, lanthanoid and the like. By applying a drug thus produced as a complex of a cationic dendrimer and a chelating agent, the carrier of the present invention can also be applied as a multimodality imaging probe.

The cationic molecule and anionic molecule to be applied to the above-mentioned drug complex is not particularly limited, and an appropriate molecule can be selected from the description of the present specification.

However, when imaging of particular lymph node is performed, it is preferable to select polyethylenimine as a cationic molecule and γ-polyglutamic acid as an anionic molecule.

The combination of drug complex/polyethylenimine/γ-polyglutamic acid renders the complex of the present invention lymph node-oriented, which enables lymph node imaging suitable for various uses depending on the nuclide for imaging contained in the drug complex.

The lymph node in the present invention is preferably the sentinel lymph node.

The sentinel lymph node is a lymph node where a cancer cell that entered from a tumor into the lymph flow first arrives, and the metastasis first occurs among the regional lymph nodes. Therefore, a biopsy of the sentinel lymph node is required to judge whether metastasis of malignant tumor to other tissue has occurred. However, since the sentinel lymph node cannot be identified with bare eyes, imaging is important for secure collection thereof.

Although several tracers have heretofore been developed to detect sentinel lymph node, the detection method is limited, and imaging by a different method sometimes produced different results due to the behavior of the tracer. Moreover, a desirable tracer in terms of migration to and retention in the sentinel lymph node has not been obtained.

The present invention is applicable to various imaging methods, is lymph node-oriented, and provides a carrier of nuclide for imaging, which can be retained particularly in the sentinel lymph node. That is, a carrier of nuclide for imaging, which contains a complex wherein an antigen or drug is a complex consisting of a nuclide for imaging, a cationic dendrimer and a chelating agent; the cationic molecule is polyethylenimine; the anionic molecule is γ-polyglutamic acid; and is lymph node (particularly sentinellymph node)-oriented, is provided.

The present invention also relates to an imaging method using the complex of the present invention.

In this case, any of the antigen or drug, cationic molecule and anionic molecule in the complex of the present invention is desirably modified to be suitable for a diagnostic apparatus (method) or imaging apparatus (method). As such modification, labeling with various nuclides (e.g., radioactive nuclide for PET, radioactive nuclide for SPECT and the like), labeling with MRI contrast agent (element having MRI contrast effect), labeling with fluorescent dye (e.g., FITC, Alexa Fluor and the like), labeling with enzyme (e.g., peroxidase and the like) and the like can be mentioned.

Particularly when imaging of sentinel lymph node is performed, a complex consisting of a nuclide for imaging, a cationic dendrimer and a chelating agent is preferably selected as an antigen or drug, polyethylenimine is preferably selected as a cationic molecule, and γ-polyglutamic acid is preferably selected as an anionic molecule. In this way, imaging of the sentinel lymph node can be performed by various imaging methods.

The present invention is explained in detail in the following by referring to Examples, which are not to be construed as limitative.

EXAMPLES

Example 1

Method

A pMSP-1/PEI/γ-PGA complex was prepared such that the charge ratio of pMSP-1, which is a pDNA encoding malaria antigen MSP-1, polyethylenimine (PEI) and γ-polyglutamic acid (γ-PGA) was 1:8:6. In addition, a pCMV-Luc/PEI/γ-PGA complex using pCMV-Luc encoding firefly luciferase having no efficacy was used as a control. The pCMV-Luc/PEI/γ-PGA complex (40 μg (A) in DNA amount) and the pMSP-1/PEI/γ-PGA complex (0.4 (B), 4 (C), 40 (D) and 80 (E) μg in DNA amount) were intravenously administered to mouse every 3 weeks, 3 times in total. Ten days after the final immunization, the mouse serum was collected, and the antibody titer to malaria was measured using ELISA. In addition, 3 weeks after the final immunization, the mouse was infected with malaria parasite, and the survival of the mouse after infection was observed with time daily.
Results The vaccine antibody titers are shown in FIG. 1. When the serum dilution was not less than 320-fold, the antibody titers showed no difference. On the other hand, when the dilution ratio was lower than that, the complex containing much pDNA amount showed a higher antibody titer. In addition, the control group did not show increase of the antibody titer.

Figure 2:
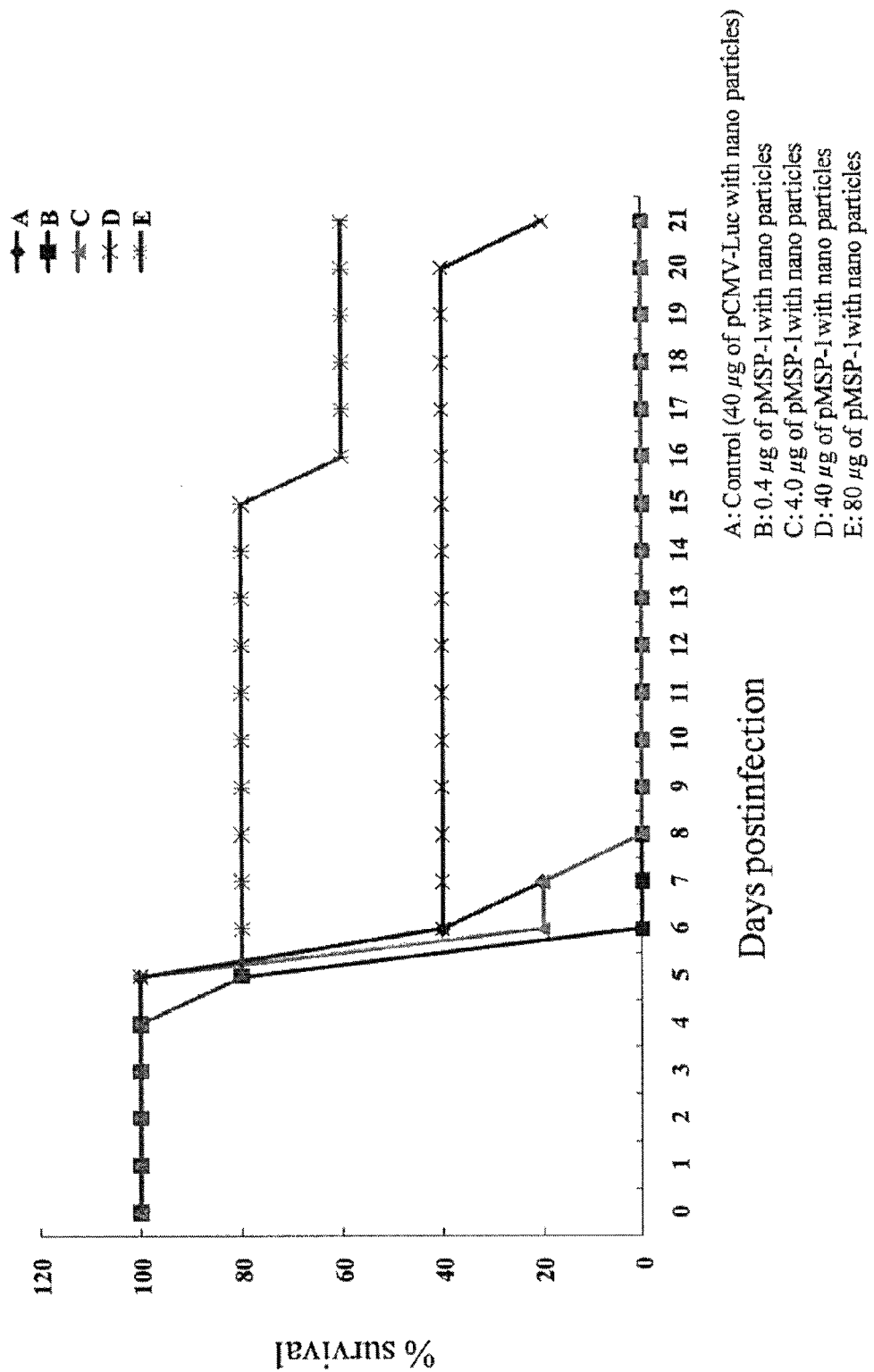
FIG. 2 shows mouse survival rates after malaria infection in Example 1.

The survival rate after malaria infection is shown in FIG. 2. When the amount of pDNA in pCMV-Luc/PEI/γ-PGA complex-administration group and pMSP-1/PEI/γ-PGA complex-administration group was up to 4 μg, the survival rate was almost 0% on day 9 postinfection, and when pDNA was 40 μg or 80 μg, the survival rate was maintained high even after day 9.

Example 2

Method

Figure 3:
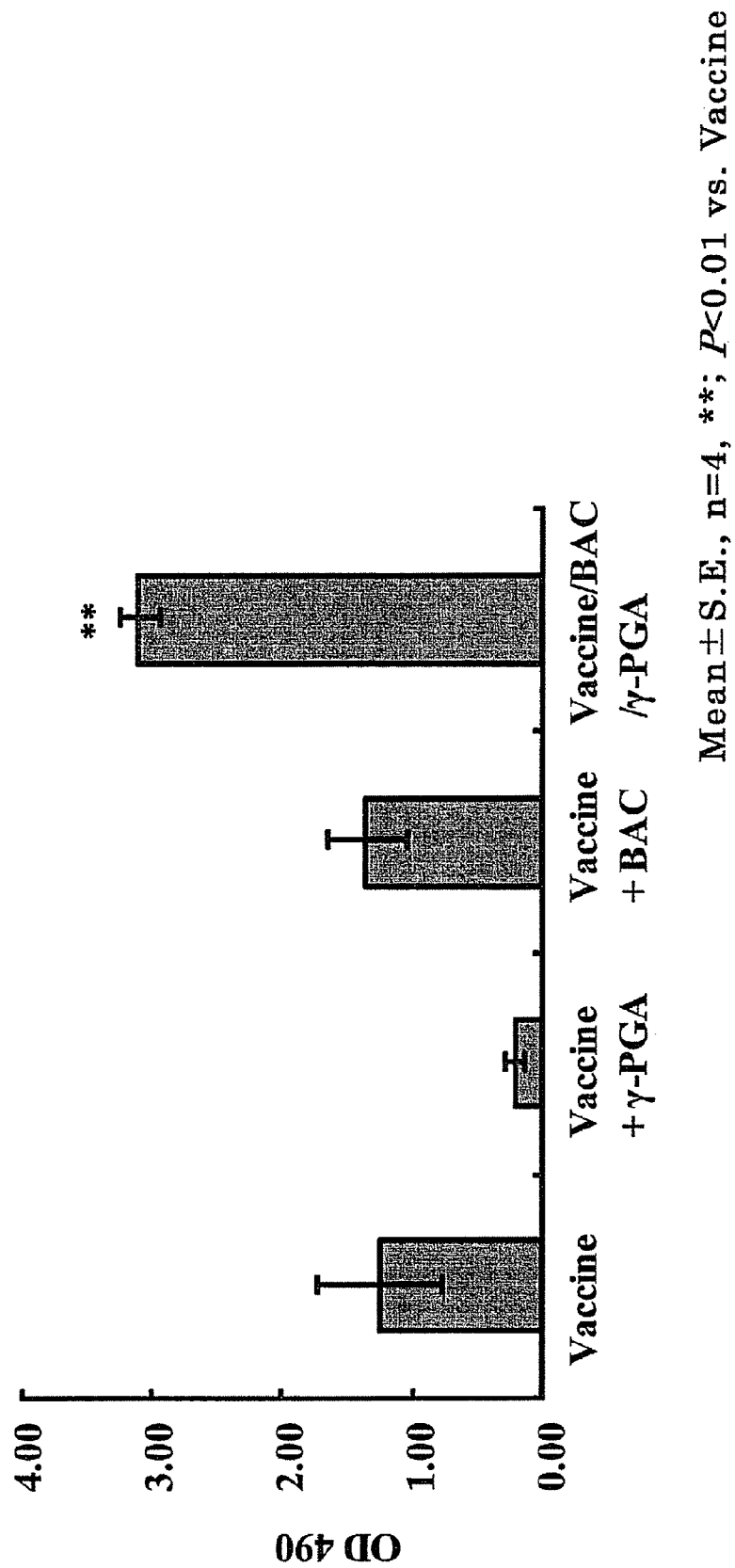
FIG. 3 shows vaccine antibody titers in Example 2.

A vaccine/BAC/γ-PGA complex wherein inactivated influenza virus (Vaccine) was microparticulated using benzalkonium chloride (BAC) and γ-PGA was prepared. Vaccine alone, a mixture of Vaccine and any of BAC and γ-PGA, or the Vaccine/BAC/γ-PGA complex was administered to mouse. Four weeks later, blood samples were collected, and the antibody titer to influenza virus was measured using ELISA.
Results FIG. 3 shows antibody production effect of each vaccine (vaccine antibody titer). Even when any of BAC and γ-PGA was mixed with Vaccine, the antibody titer showed no significant difference from Vaccine alone; however, the Vaccine/BAC/γ-PGA complex showed a significantly high antibody titer as compared to Vaccine alone.

Example 3

Method

As a model protein, bovine serum albumin (BSA) was fluorescently labeled with rhodamine B isothiocyanate and used. A BSA/BAC/γ-PGA complex prepared using benzalkonium chloride (BAC) and γ-PGA with BSA or BSA was added to a dendritic cell line, DC2.4 cell, and the mixture was incubated for 2 hr. The cells were washed and fluorescence images of the cell were measured by a fluorescence microscope 22 hr later.
Results The fluorescence microscopic observation images of the cell are shown in FIG. 4. Although cellular uptake was not observed with BSA alone, fluorescence of BSA was intensively observed in the cell added with the BSA/BAC/γ-PGA complex, which clarifies that the BSA/BAC/γ-PGA complex shows high cellular uptake by dendritic cell.

Example 4

Method

Figure 5:
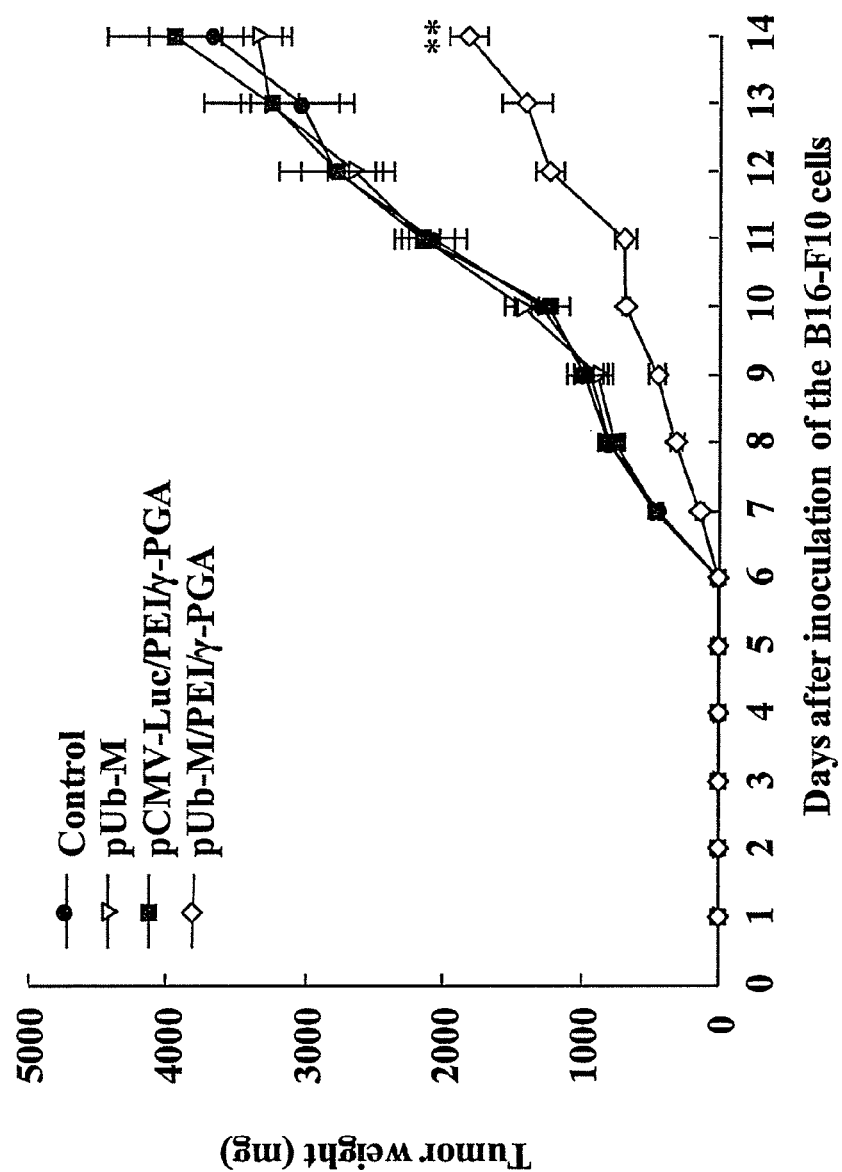
FIG. 5 shows changes in the tumor weight in Example 4.

A pUb-M/PEI/γ-PGA complex was prepared such that the mixing ratio (charge ratio) of pUb-M, which is a pDNA encoding a ubiquitinated epitope of gp100 and TRP-2, as a melanoma antigen gene, PEI and γ-PGA was 1:8:6. To C57BL mice were administered 5% sugar solution (control) or pUb-M alone, and pCMV-Luc/PEI/γ-PGA complex prepared using pCMV-Luc having no efficacy, PEI and γ-PGA and pUb-M/PEI/γ-PGA complex, every 2 weeks, 4 times in total to induce immunity. Two weeks after the final immunization, melanoma cell line B16-F10 cell, or a B16-F10-Luc cell constitutively expressing luciferase was intradermally or intravenously administered, whereby an intradermal transplantation model and a lung metastasis model were prepared, respectively. The tumor diameter of the intradermal transplantation model was measured daily. In addition, the lung was isolated on day 21 from the preparation of the lung metastasis model, observed, the luciferase activity of the lung was measured, and the lung metastatic cell number was calculated.
Results Changes of the tumor weight of intradermally transplanted malignant melanoma are shown in FIG. 5. While the tumor growth in the mice administered with pUb-M alone or the pCMV-Luc/PEI/γ-PGA complex showed no significant difference from the control group; however, the tumor growth of the mouse administered with the pUb-M/PEI/γ-PGA complex showed a significantly low value as compared to the control group.

Figure 6:
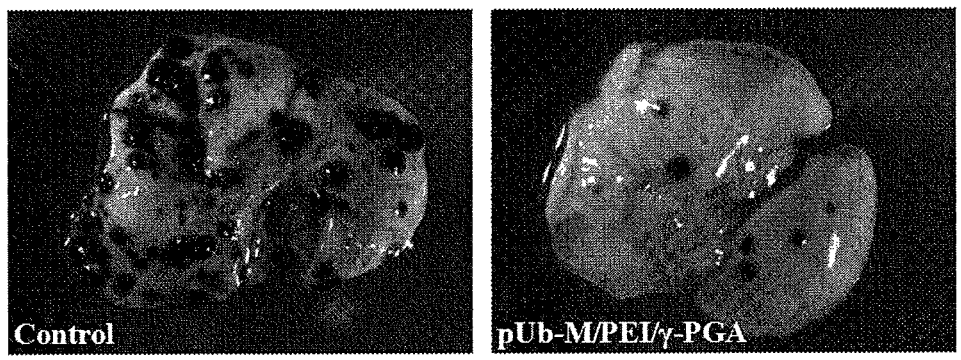
FIG. 6 shows lung metastasis of the malignant melanoma in Example 4.
Figure 7:
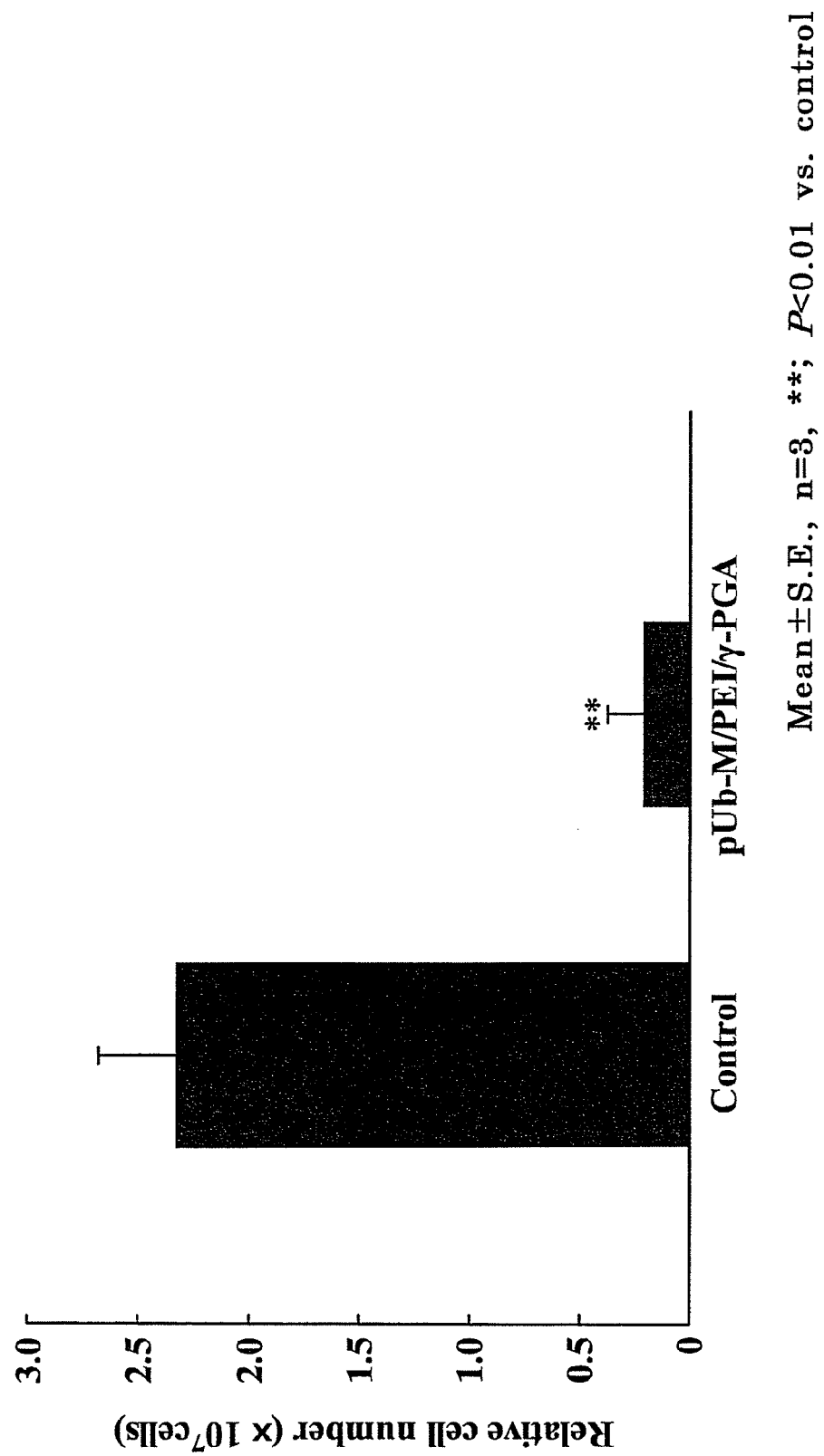
FIG. 7 shows cell number that showed lung metastasis in Example 4.

The lung metastasis of the intravenously injected malignant melanoma is shown in FIG. 6. In addition, the lung metastatic cell number is shown in FIG. 7. As compared to the 5% sugar solution administration group (control), the pUb-M/PEI/γ-PGA complex administration group showed a remarkable suppression of lung metastasis.

Example 5

Method pDNA (pCMV-Luc) and PEI were mixed to prepare a pDNA/PEI complex. In addition, to this pDNA/PEI complex was added N-[1-(2,3-dioleyloxy)propyl]-N,N,N-trimethylammonium (DOTMA), and N-lauroylsarcosine (LS) was further added to prepare a novel drug delivery complex. Respective complexes were prepared such that the mixing ratio (charge ratio) of pDNA, PEI, DOTMA and LS was 1:2:0:0, 1:2:2:0, 1:2:2:2 or 1:2:2:4, and the particle size and surface charge were measured. Furthermore, complexes having the mixing ratios (charge ratios) of 1:2:2:0, 1:2:2:2 and 1:2:2:4 were respectively administered to mouse from the tail vein, and the gene expression of the liver, spleen and lung was measured 6 hr later. In addition, a 1:8:0:0 complex was used as a control.

Complexes having the mixing ratios (charge ratios) of 1:8:0:0 and 1:2:2:2 were administered to mice, and the gene expression was observed using an in vivo imaging apparatus.

In addition, complexes having various mixing ratios (charge ratios) were prepared, and the contribution rate on the gene expression level of each component in the lung was measured using multivariate analysis.

Results

Figure 8:
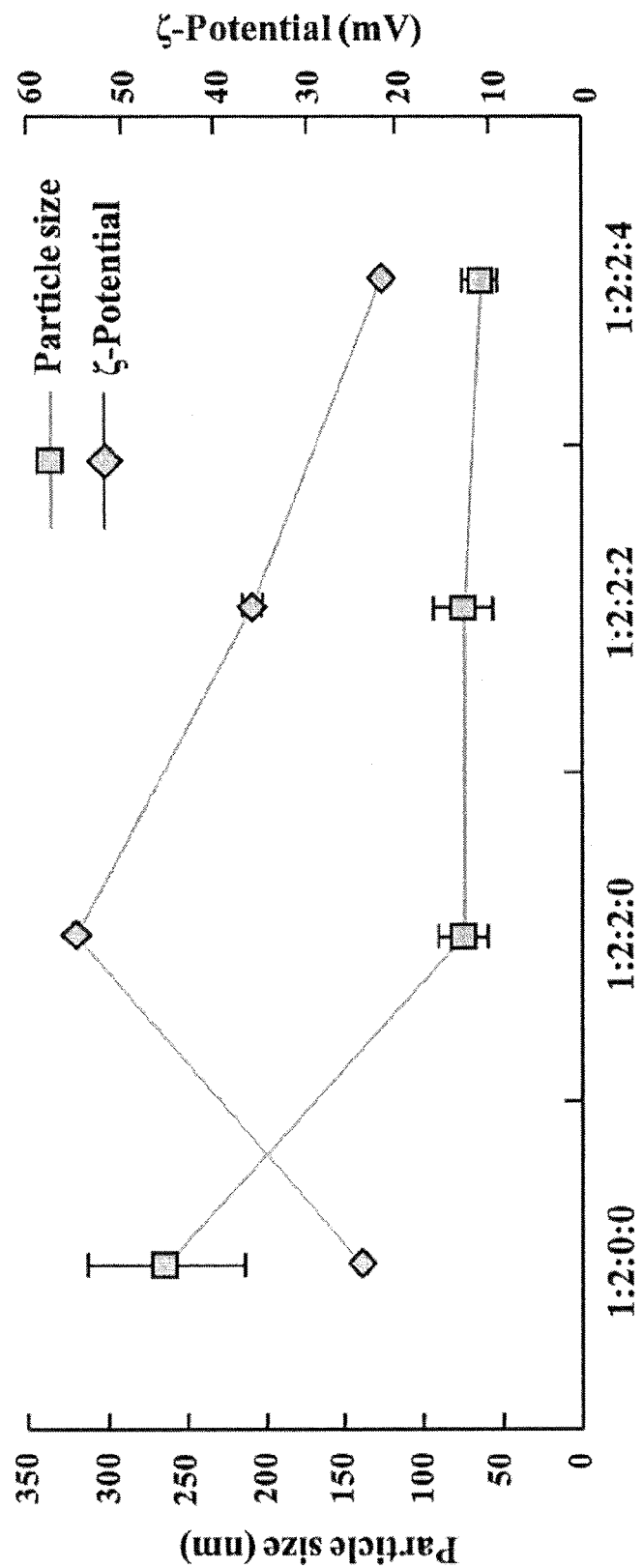
FIG. 8 shows particles size and surface charge in Example 5.

The particles size and surface charge are shown in FIG. 8. The particle size was almost the same even after addition of LS, and the surface charge was confirmed to come closer to the negative charge by the addition of LS.

Figure 9:
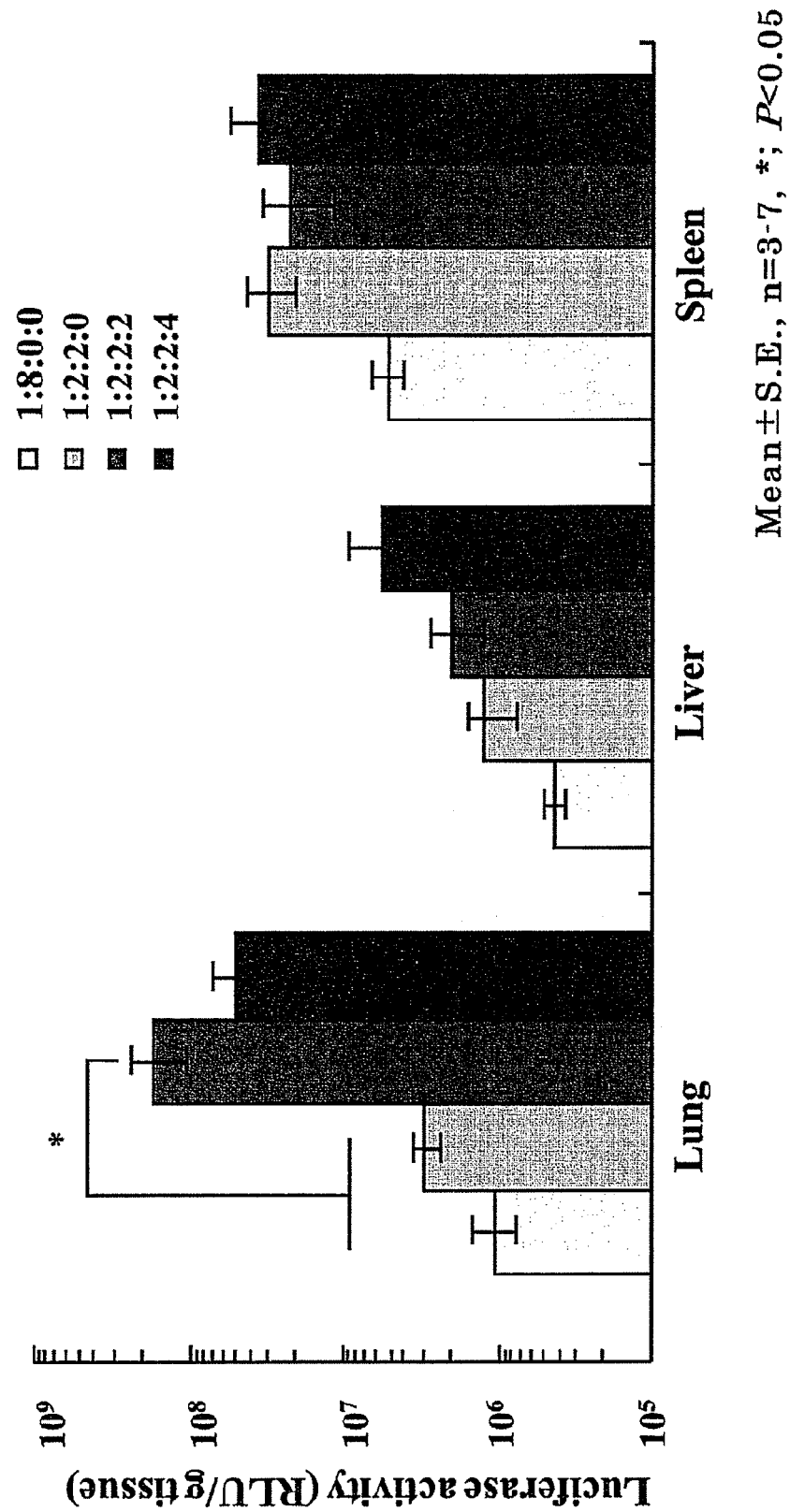
FIG. 9 shows gene expression (luciferase activity) in Example 5.

The luciferase activity is shown in FIG. 9. Addition of LS markedly increased the gene expression level in the lung.

The mouse imaged with luciferase is shown in FIG. 10. The complex added with LS was confirmed to show high expression of luciferase in the lung.

Figure 11:
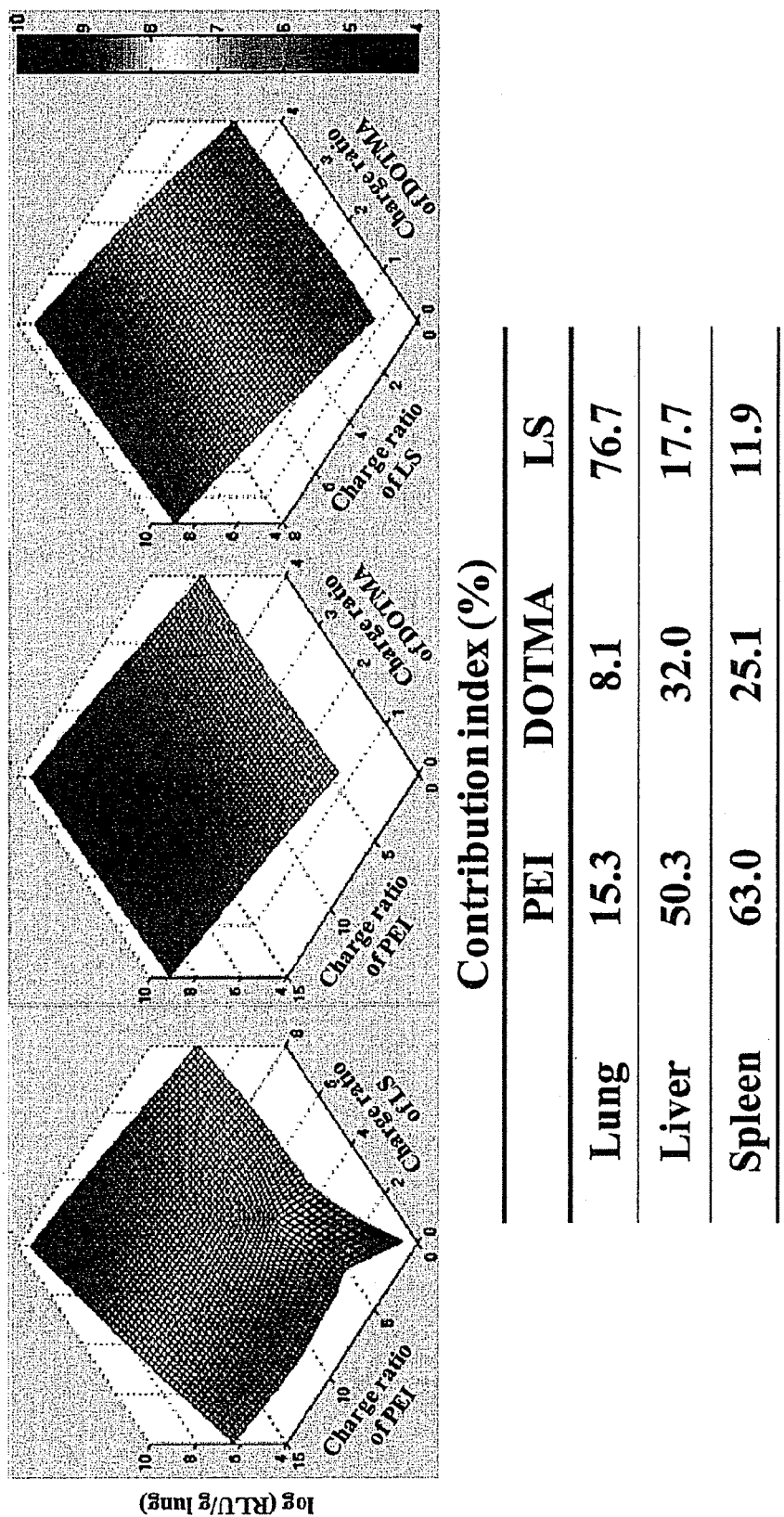
FIG. 11 shows the spline interpolation methods and contribution indices of multivariates in Example 5.

The multivariate spline interpolation method and the contribution index are shown in FIG. 11. This has clarified that LS contributed most to the delivery to the lung.

Example 6

Method

Liposome consisting only of phosphatidylserine (DOPS) was prepared. To a pDNA/PEI complex prepared using pCMV-Luc was added the DOPS liposome such that the mixing ratio (charge ratio) of pDNA, PEI and DOPS was 1:8:6 to prepare a pDNA/PEI/DOPS complex. The pDNA/PEI complex and pDNA/PEI/DOPS complex were intravenously administered to mice, and the gene expression level of each organ was measured 6 hr later.

Results

Figure 12:
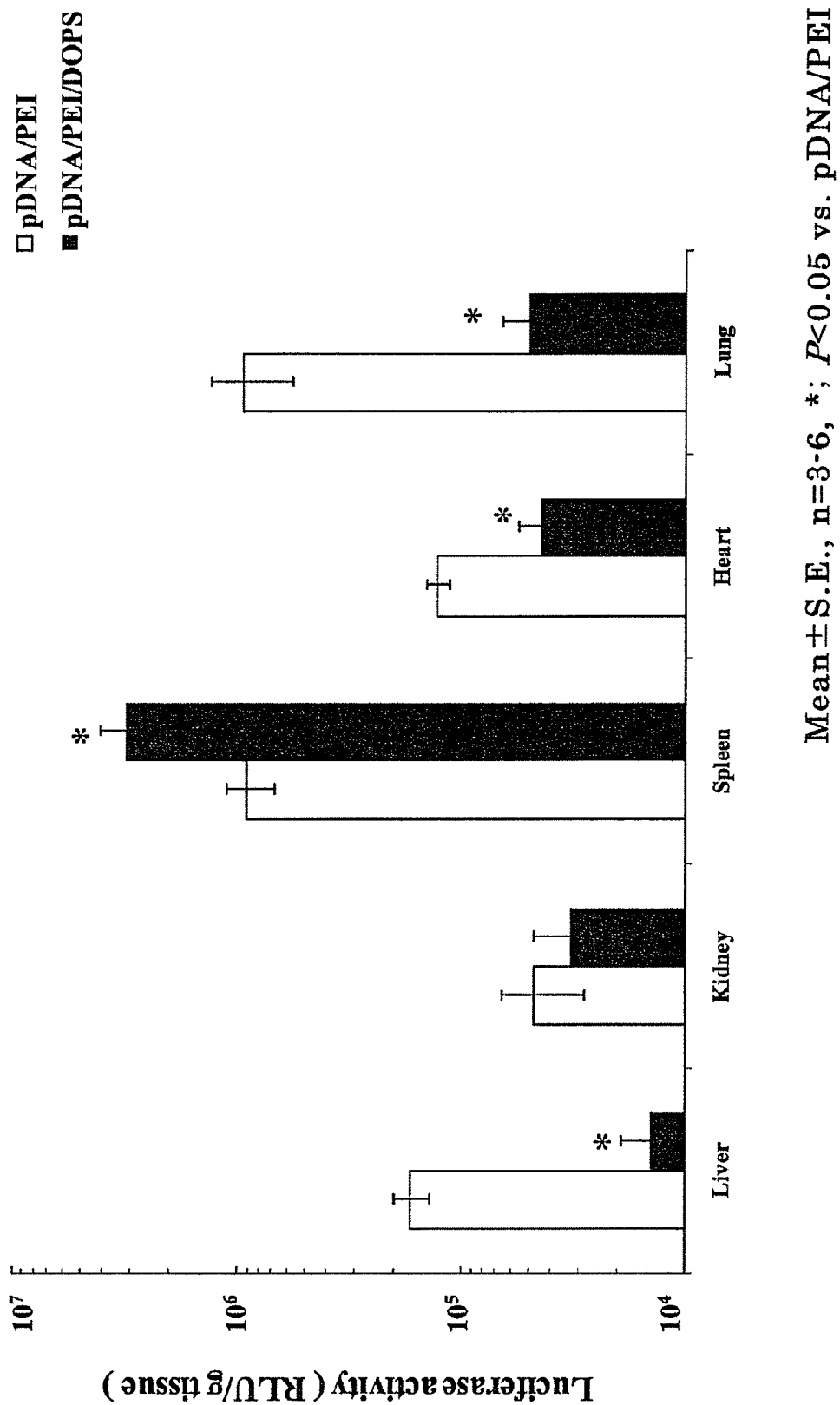
FIG. 12 shows gene expressions (luciferase activities) in Example 6.

The gene expression (luciferase activity) of each organ is shown in FIG. 12. The pDNA/PEI/DOPS complex was clarified to show a particularly high gene expression effect on the spleen as compared to the pDNA/PEI complex.

Example 7

Method

In addition to an aptamer recognizing cancer surface antigen MUC1, an aptamer having a non-specific sequence was used. A pDNA/PEI complex was prepared such that the charge ratio of pCMV-Luc and polyethylenimine was 1:8. An aptamer was added to the pDNA/PEI complex such that the mixing ratios (charge ratios) of pDNA, PEI and the aptamer were 1:8:1.25, 1:8:2.5, 1:8:5 and 1:8:10 to prepare pDNA/PEI/aptamer complexes, and the particle size and surface charge were measured. In addition, the gene expression level of the complex having the charge ratio of 1:8:10 in A549 cell (MUC1+) was measured.

A pDNA/PEI complex was prepared such that the charge ratio of pDNA and PEI was 1:8. An antibody to STEAP-4 (six-transmembrane epithelial antigen of the prostate-4: adipocyte membrane protein) was added at 200, 300 and 400 μg to a 10 μg pDNA-containing pDNA/PEI complex to prepare pDNA/PEI/antibody complexes, and the particle size and surface charge were measured.

Results

Figure 13:
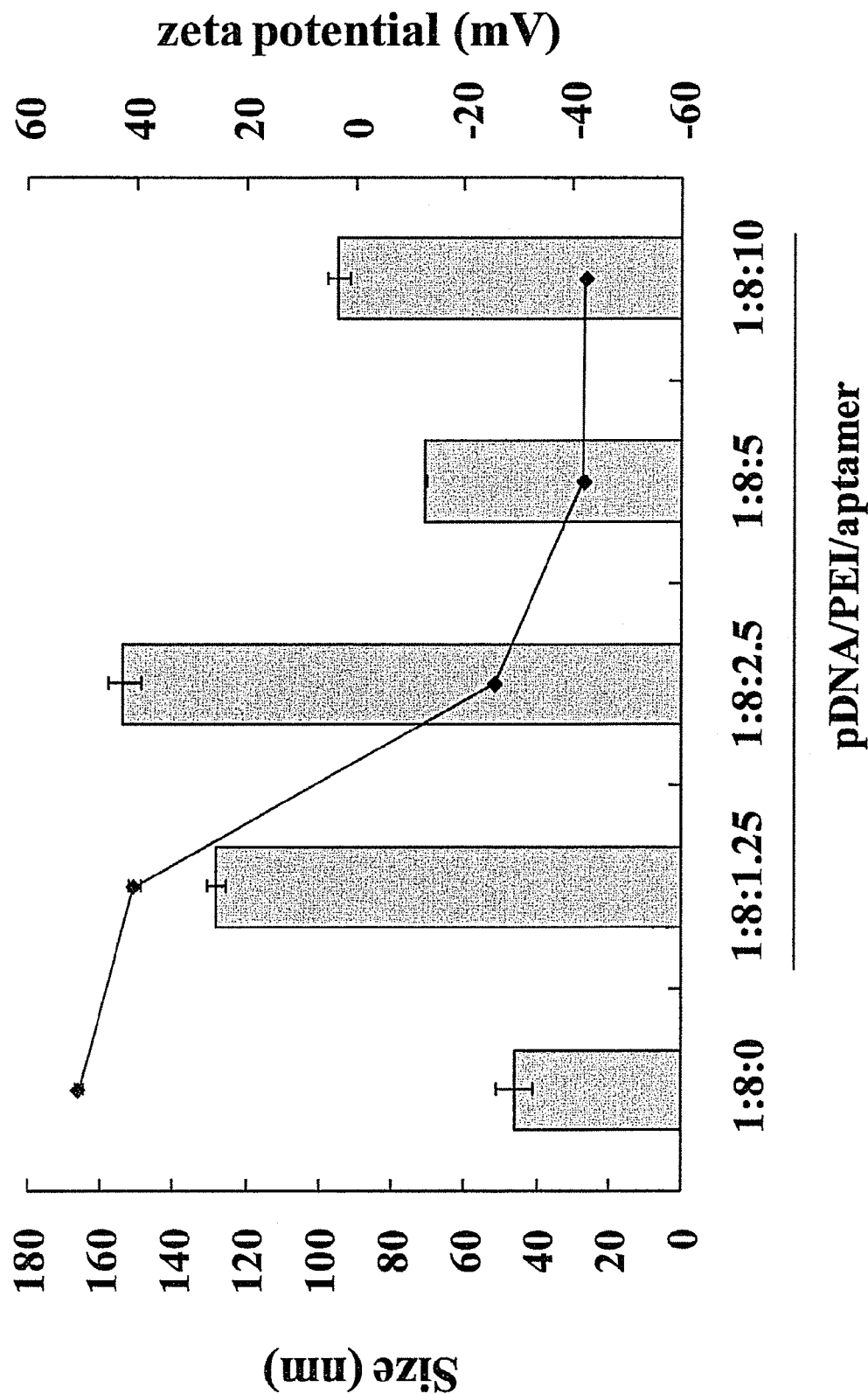
FIG. 13 shows the particles size and surface charge in Example 7.

The particles size and surface charge of the complexes coated with the aptamer are shown in FIG. 13. When the mixing ratio (charge ratio) of the pDNA/PEI/aptamer complex was 1:8:10, a most preferable complex having a small particle size and a negative surface charge was obtained.

Figure 14:
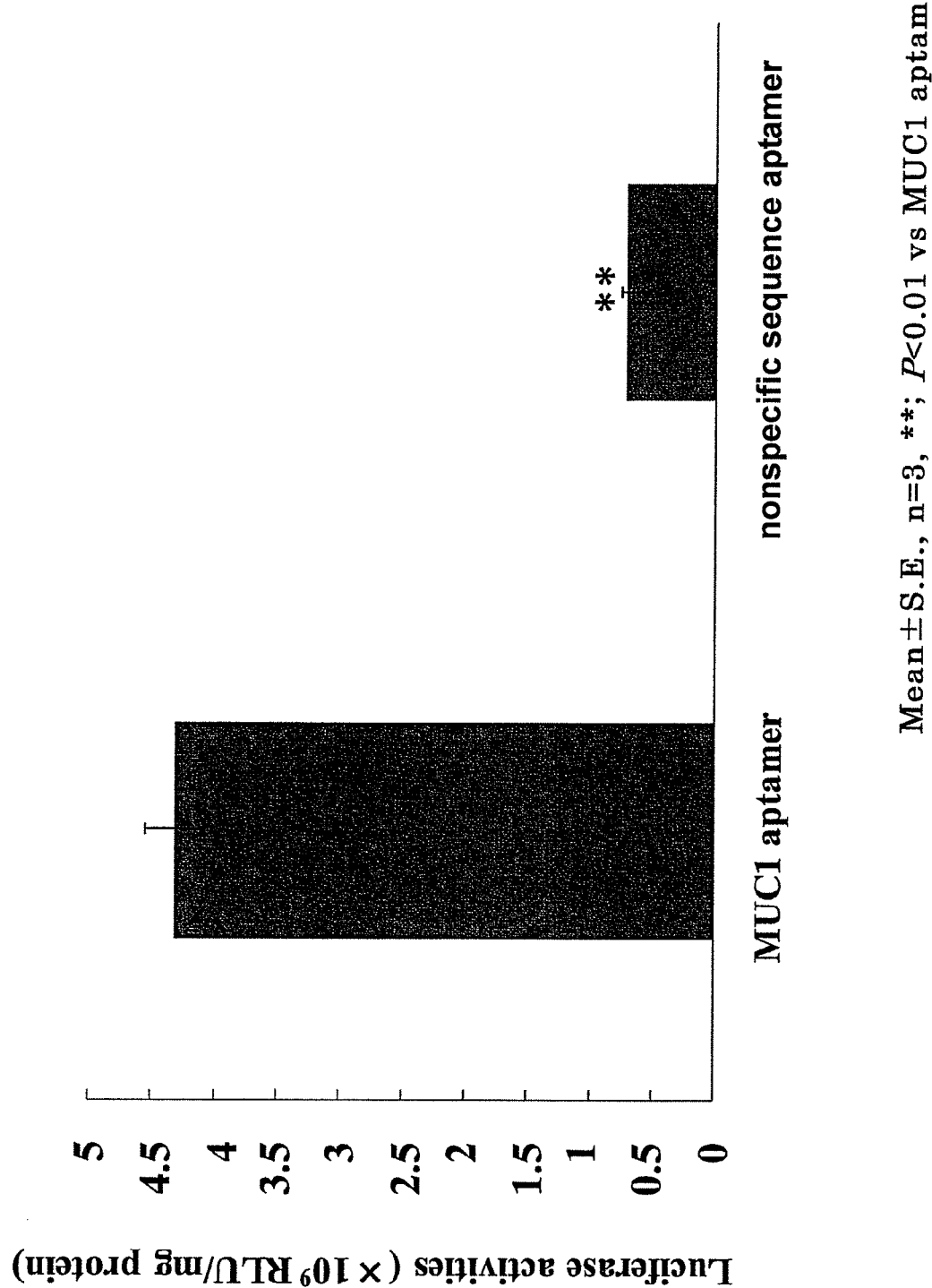
FIG. 14 shows gene expressions (luciferase activities) in Example 7.

The luciferase activity in the MUC1-expressing cell is shown in FIG. 14. In the A549 cell expressing MUC1, the complex coated with an aptamer to MUC1 showed a remarkably high luciferase activity as compared to the non-specific aptamer.

Figure 15:
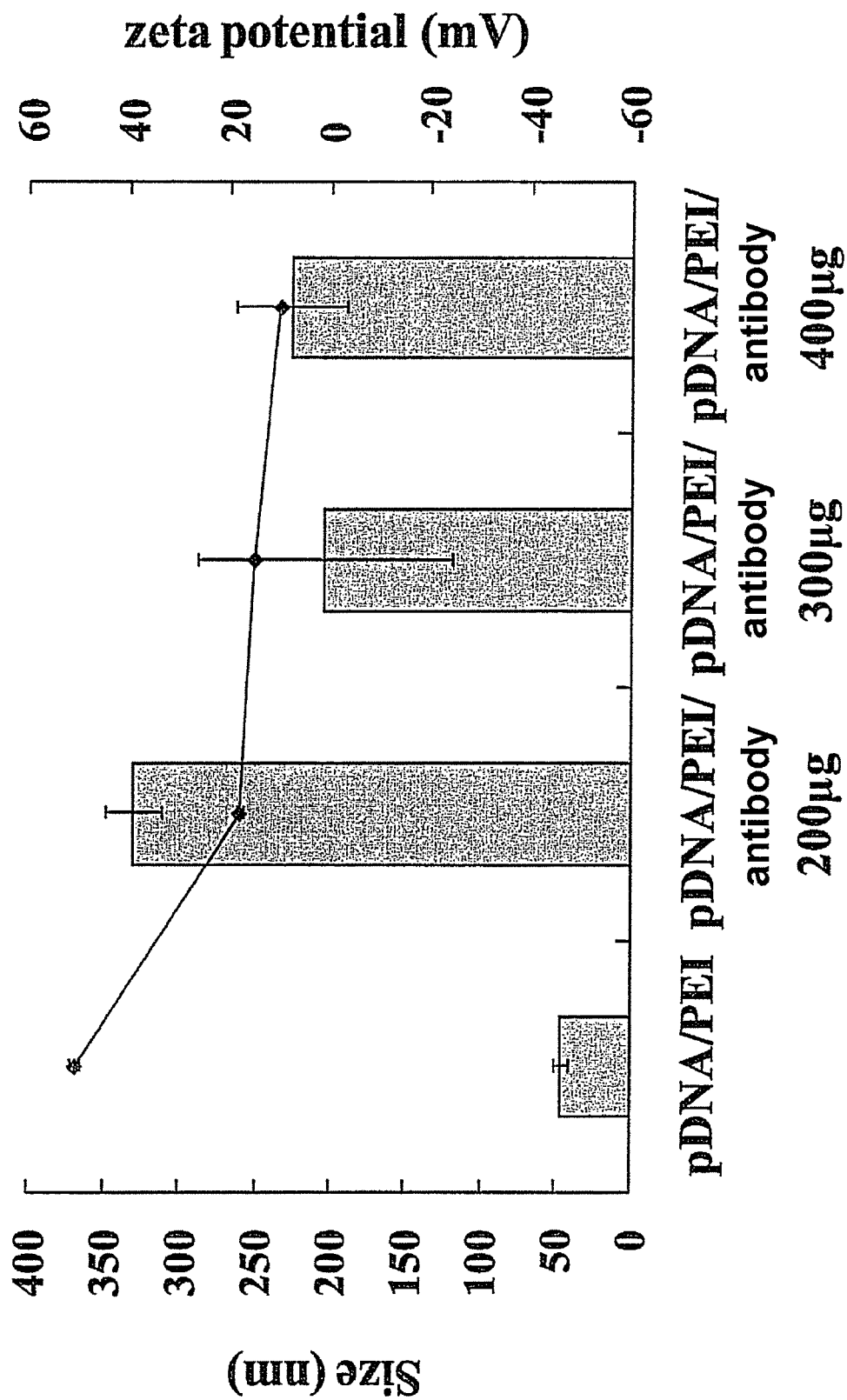
FIG. 15 shows particles sizes and surface charges in Example 7.

The particles size and surface charge of the complex coated with the antibody are shown in FIG. 15. The particles size was the smallest when the antibody was 300 μg, and the surface charge showed no difference between the complexes coated with the antibody. Therefore, the complex of pDNA/PEI/antibody (300 μg) was considered to be most suitable.

Example 8

Method

To the pDNA/PEI complex prepared using pCMV-Luc was added glycyrrhizin such that the mixing ratio (charge ratio) of pDNA, PEI and GLY was 1:8:12 to prepare a pDNA/PEI/GLY complex. A pDNA/PEI complex (commercially available gene vector) and the pDNA/PEI/GLY complex (novel gene vector) were intravenously administered to mice, and gene expression level of each organ was measured 6 hr later.

Results

Figure 16:
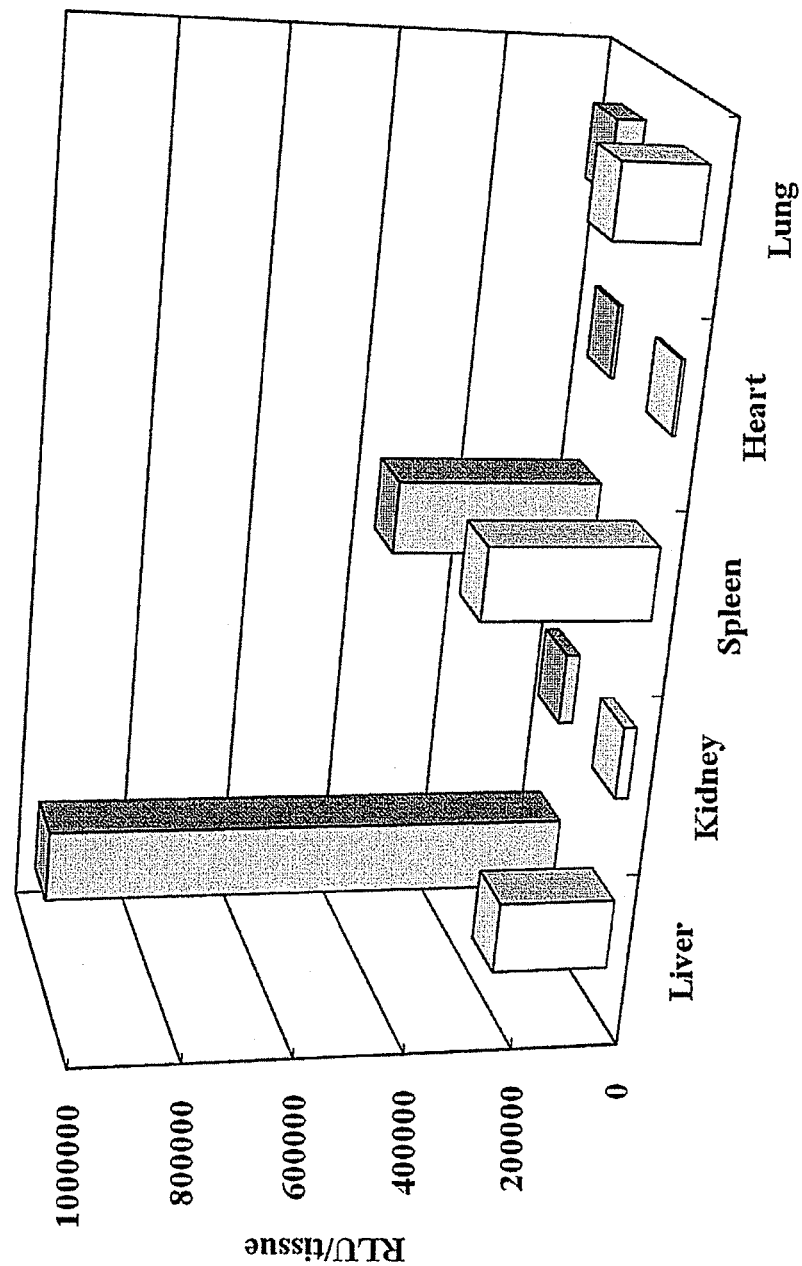
FIG. 16 shows gene expressions (luciferase activities) in Example 8.

The gene expression (luciferase activity) in each organ is shown in FIG. 16. The pDNA/PEI/GLY complex was clarified to show a particularly high gene expression effect on the liver as compared to the pDNA/PEI complex.

Example 9

Method

Inactivated influenza virus fluorescently labeled with a fluorescent dye (hereinafter Vaccine) was self-assembled with benzalkonium chloride (BK) and γ-PGA to prepare Vaccine/BAC/γ-PGA complex, and added to dendritic cell line (DC2.4).

Results

The uptake of the inactivated virus and the antibody titer of mice are shown in FIG. 17. With the virus alone, uptake into a dendritic cell was not observed; however, the Vaccine/BAC/γ-PGA complex greatly increased the uptake amount.

Example 10

Method

To a pDNA/PEI complex prepared using pCMV-Luc was added γ-PGA such that the mixing ratio (charge ratio) of pDNA, PEI and γ-PGA was 1:8:6 to prepare a pDNA/PEI/γ-PGA complex. To a dendritic cell line DC2.4 cell were added pDNA alone, pDNA+γ-PGA, the pDNA/PEI/γ-PGA complex, and a complex of Lipofectin and pDNA as a commercially available gene vector, and the luciferase activity was measured 22 hr later.

Results

Figure 18:
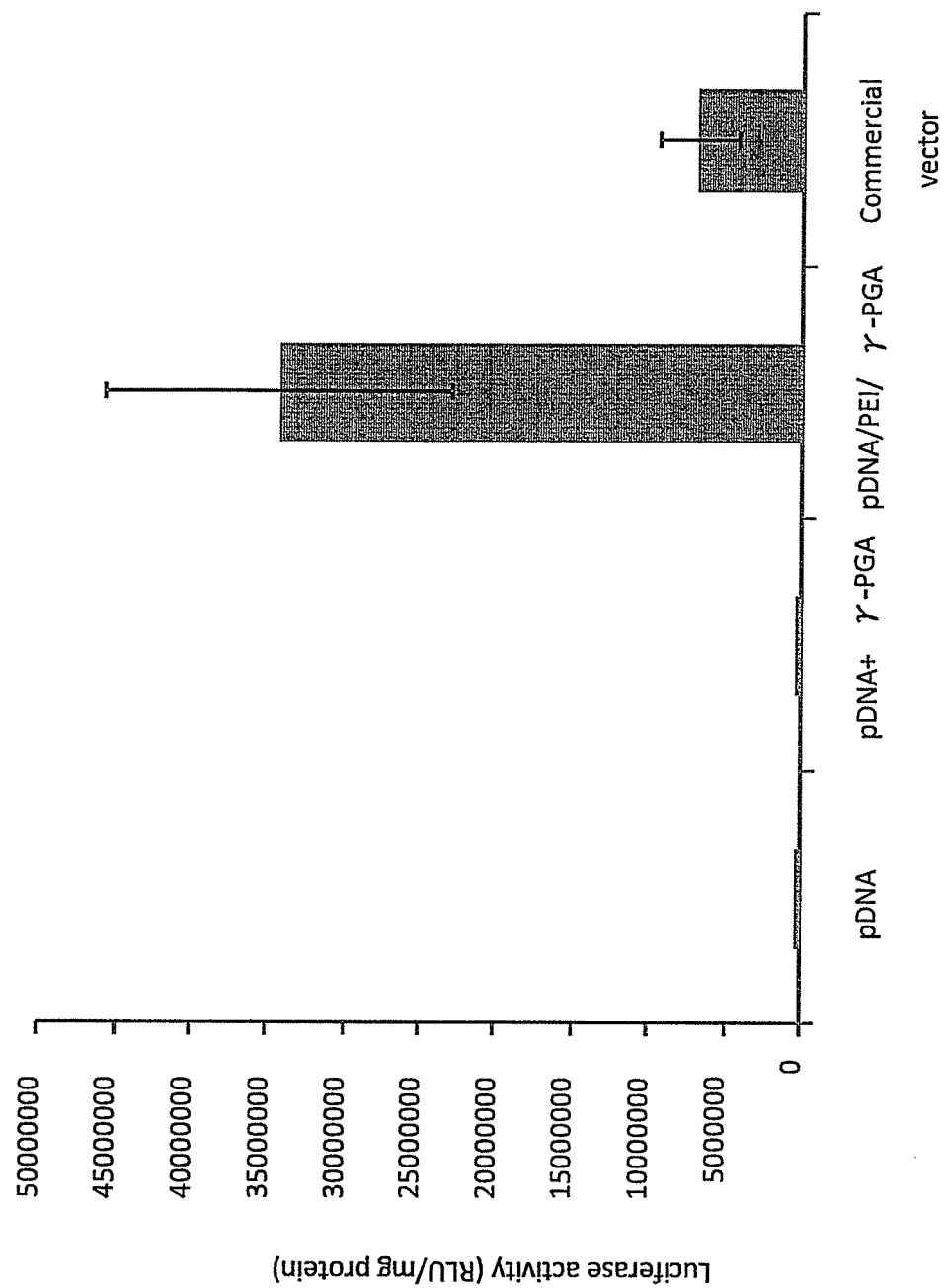
FIG. 18 shows gene expressions (luciferase activities) in Example 10.

The gene expression (luciferase activity) in the dendritic cell line is shown in FIG. 18. While gene expression was not achieved by the addition of pDNA alone, or pDNA and γ-PGA, the pDNA/PEI/γ-PGA complex showed a remarkably high gene expression effect as compared to the commercially available gene vector.

Example 11

Method

For a test to determine which complex functions most on siRNA, a gene suppression test with the luciferase activity as an index was performed. The colorectal cancer cell line colon26 cell that showed constitutive expression of luciferase was used. As siRNA, siRNA to luciferase was mixed with a commercially available gene vector, Lipofectamine RNAimax or PEI, polyarginine (PLA), DOTMA-Chol liposome, DOTMA-DOPE liposome, DC-Chol-EggPC liposome, DC-Chol-DOPE liposome to prepare cationic complexes. γ-PGA was further added, and each anionic complex was constructed. Each complex was added to the cell, and the luciferase activity was measured 22 hr later. The value was calculated with the luciferase activity of the untreated cell as 100%.

Results

Figure 19:
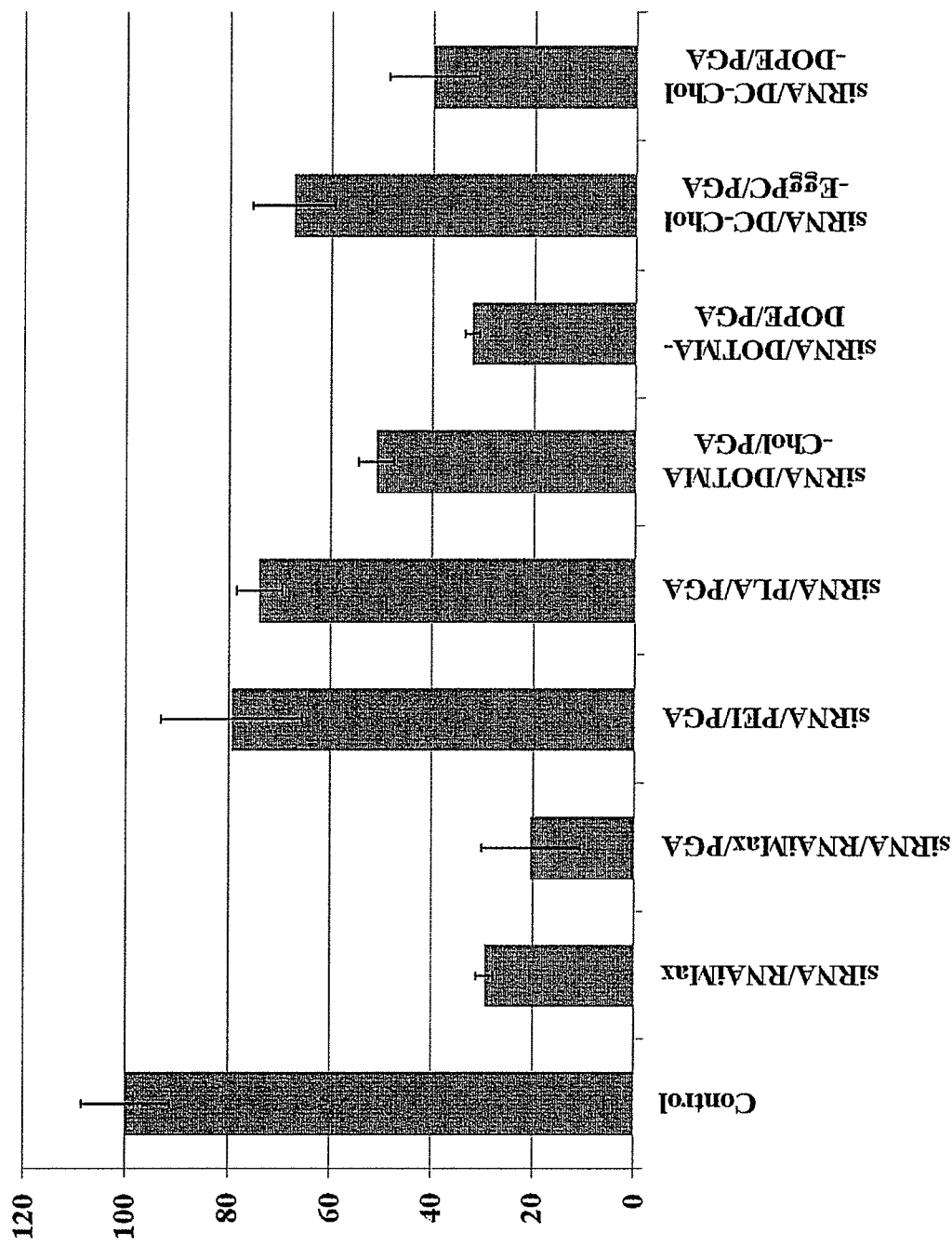
FIG. 19 shows gene suppression efficiency in Example 11.
Figure 20:
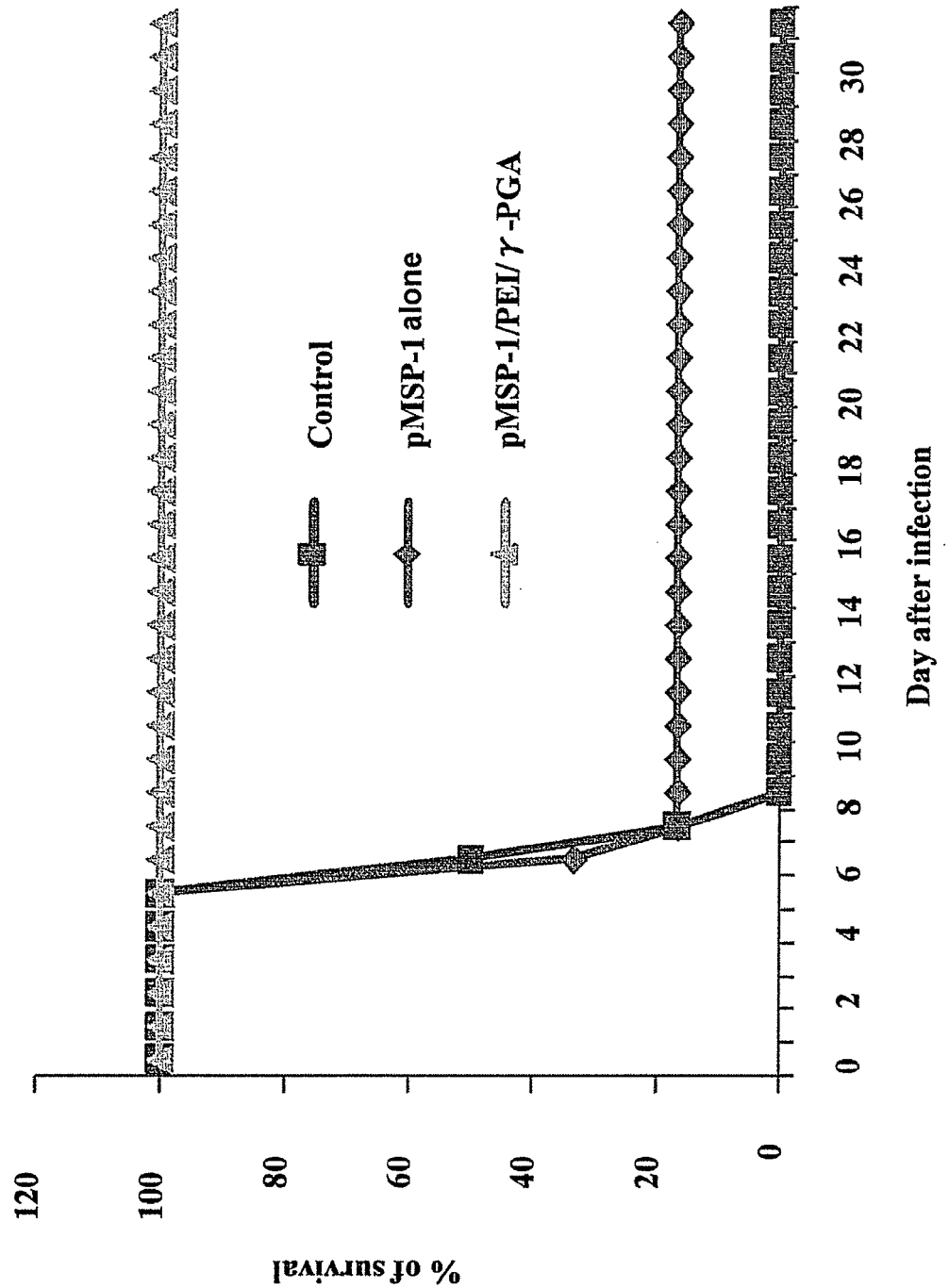
FIG. 20 shows mouse survival rates after malaria infection in Example 12.

Gene suppression efficiency with the luciferase activity as an index is shown in FIG. 19. As a result of the study of various cationic polymers and liposomes, for siRNA, a liposome was suitable as a cationic molecule rather than a polymer. Moreover, a complex of a liposome containing DOPE (a membrane fusion lipid) and siRNA was covered using γ-PGA, whereby a vector permitting targeting while showing an effect comparable to that of a commercially available siRNA vector could be developed.

Example 12

Method

In the same manner as in Example 1 except the dose (as DNA amount) of the complex was increased to 100 µg, malaria DNA vaccine (pMSP-1) alone or a pMSP-1/PEI/γ-PGA complex was administered to mice every 3 weeks, 3 times in total, and the mice were infected with malaria parasite on day 10 from the final immunization.

Results

The survival rate of the mice after malaria infection is shown in FIG. 12. With DNA vaccine alone, a malaria infection suppressive effect was scarcely obtained; however, administration of the pMSP-1/PEI/γ-PGA complex enabled 100% suppression of malaria infection.

Example 13

Method

OVA/BK/γ-PGA complex was constructed using ovalbumin (OVA), benzalkonium chloride (BK) and γ-PGA. OVA alone, benzalkonium chloride and γ-PGA (vector alone), and OVA/BK/γ-PGA complex were administered to mice every other week, 4 times in total for immunization. After 2 weeks from the final immunization, the serum was collected, and the antibody titer to OVA was measured by ELISA. For the measurement of the antibody titer, an HRP-labeled goat-derived anti-mouse IgG antibody was used as the secondary antibody.

Results

Figure 21:
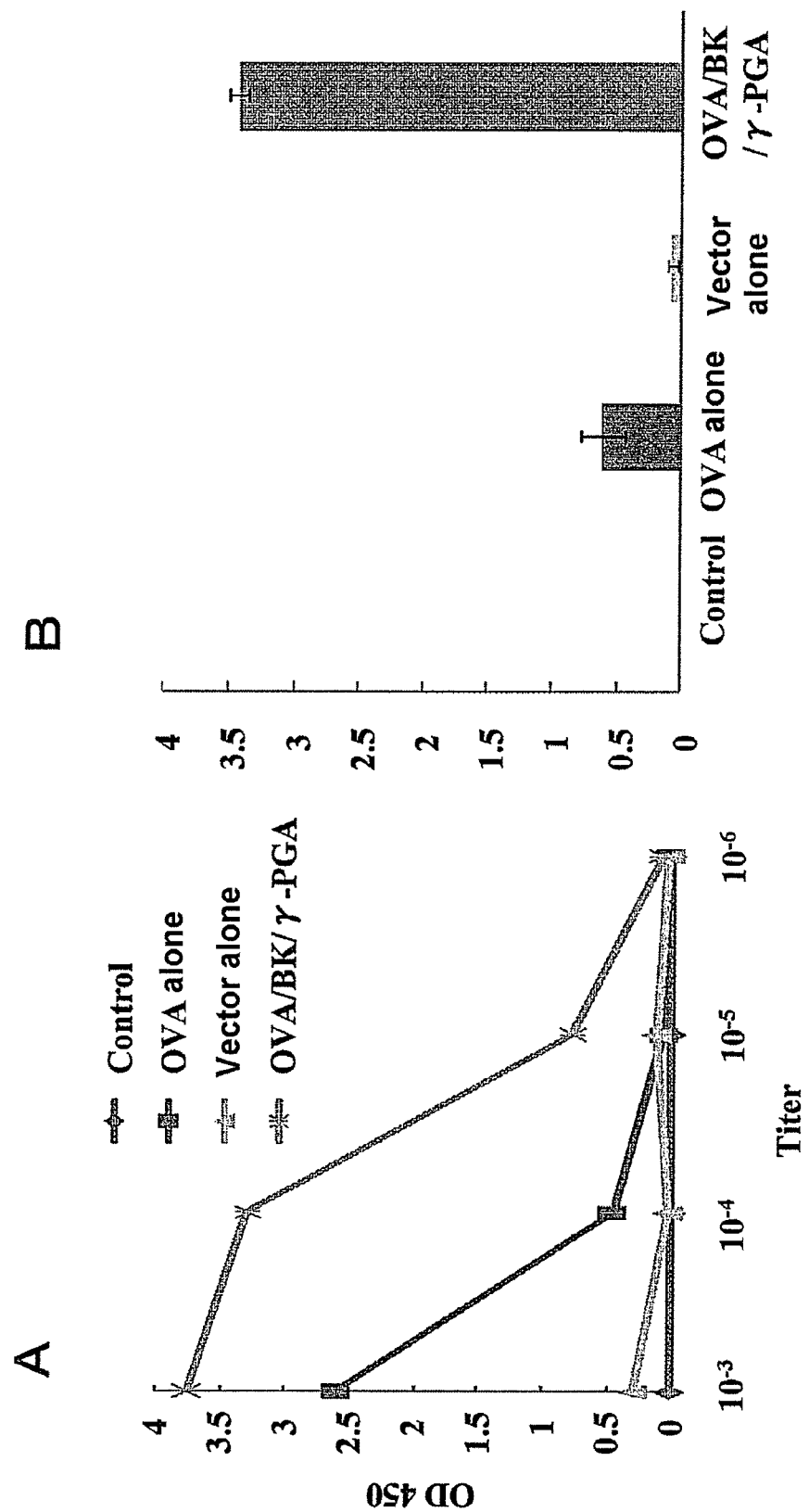
FIG. 21 shows A: variation of antibody titer by diluting mouse serum in Example 13, B: antibody titer of mouse at dilution rate $10^{-4}$.

The antibody titer in the mouse serum is shown in FIG. 21 (A: variation of antibody titer when serum is diluted, B: antibody titer of serum at dilution rate oft $10^{-4}$). OVA alone and the mixture of BK and γ-PGA did not show an immunity induction effect; however, the OVA/BK/γ-PGA complex prepared using benzalkonium chloride and γ-PGA showed a high humoral immunity induction effect.

Example 14

Method

OVA/BK/γ-PGA complex was constructed using ovalbumin (OVA), benzalkonium chloride (BK) and γ-PGA. To the mice were administered OVA alone, benzalkonium chloride and γ-PGA (vector alone), and OVA/BK/γ-PGA complex every other week, 4 times in total. After 2 weeks from the final immunization, OVA-expressing cancer cell (EG7) was intradermally transplanted, and the tumor growth after transplantation was observed.

Results

Figure 22:
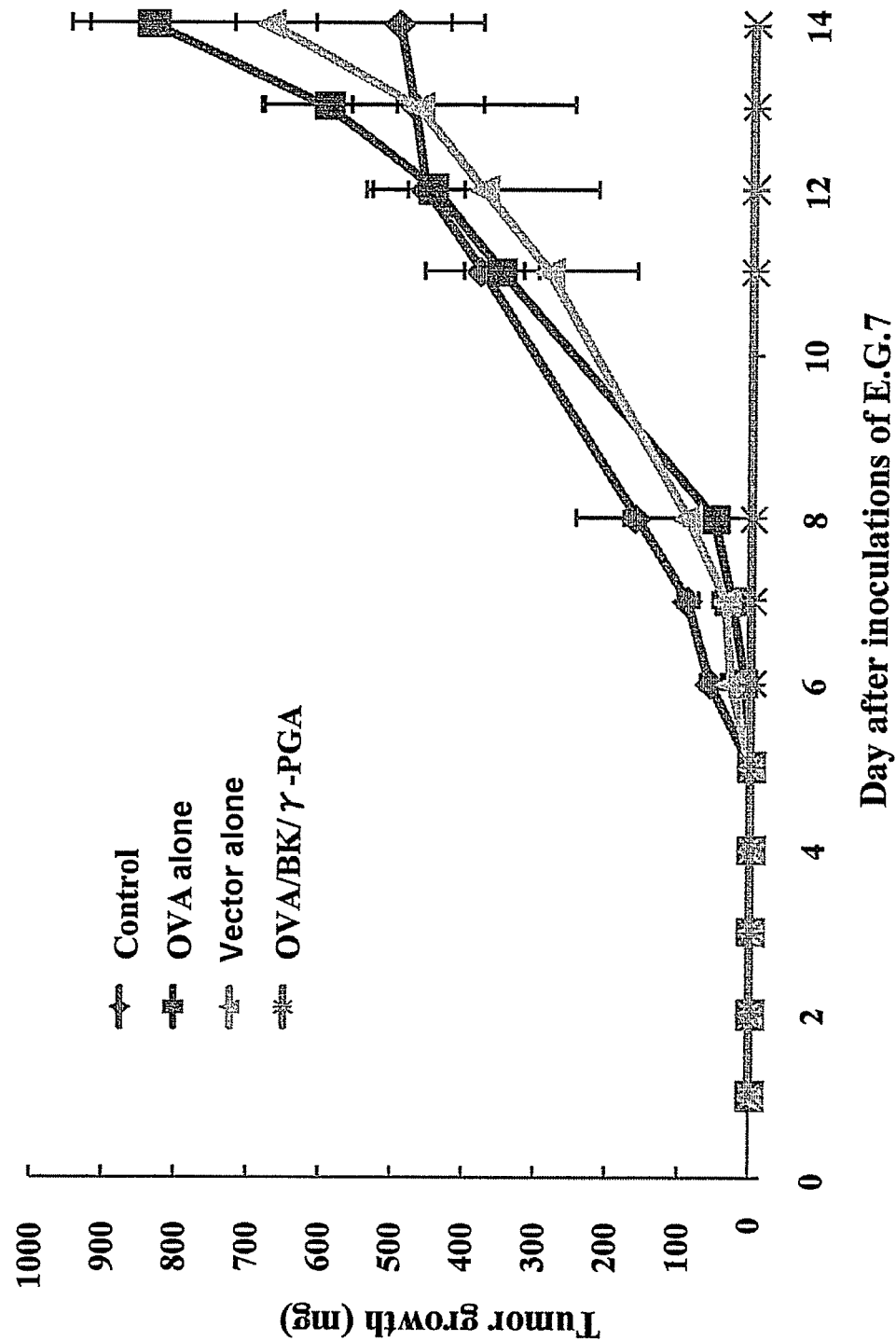
FIG. 22 shows changes of tumor growth in Example 14.

The observation results of the tumor growth from EG7 tumor transplantation are shown in FIG. 22. OVA alone and the mixture of BK and γ-PGA did not show a tumor growth suppressive effect; however, the mouse administered with the OVA/BK/γ-PGA complex could completely suppress OVA-expressing cancer cell by a high immunity induction effect.

Example 15

Method

G4-DTPA introduced with about 53 DTPAs per molecule of G4 was synthesized by reacting polyamideamine dendrimer (G4) with p-SCN benzyl diethylenetriamine pentaacetic acid (DTPA). This was mixed with PEI to give PEI/G4-DTPA, which was mixed with γ-PGA to prepare γ-PGA/PEI/G4-DTPA. A $^{111}$In-labeled form was prepared by a similar method and using G4-DTPA-$^{111}$In. The particle size and the zeta potential were measured. As a result, the production of PEI/G4-DTPA having membrane potential 47.7±6.0 mV, particle size 30.2±3.2 nm and γ-PGA/PEI/G4-DTPA having membrane potential −48.9±1.6 mV, particle size 24.8±3.7 nm was confirmed. As a comparison control, ALG/PEI/G4-

DTPA containing alginic acid (ALG), which is a different anionic polymer, and its $^{111}$In-labeled form were also prepared by a similar operation.

PEI/G4-DTPA, γ-PGA/PEI/G4-DTPA and ALG/PEI/G4-DTPA were added to RAW264, and the cytotoxicity was evaluated. Moreover, each complex was administered from the foot pad of a male rat. The radioactivity of each organ was measured over time, and distribution of each particle in the body was evaluated.

Results

Figure 23:
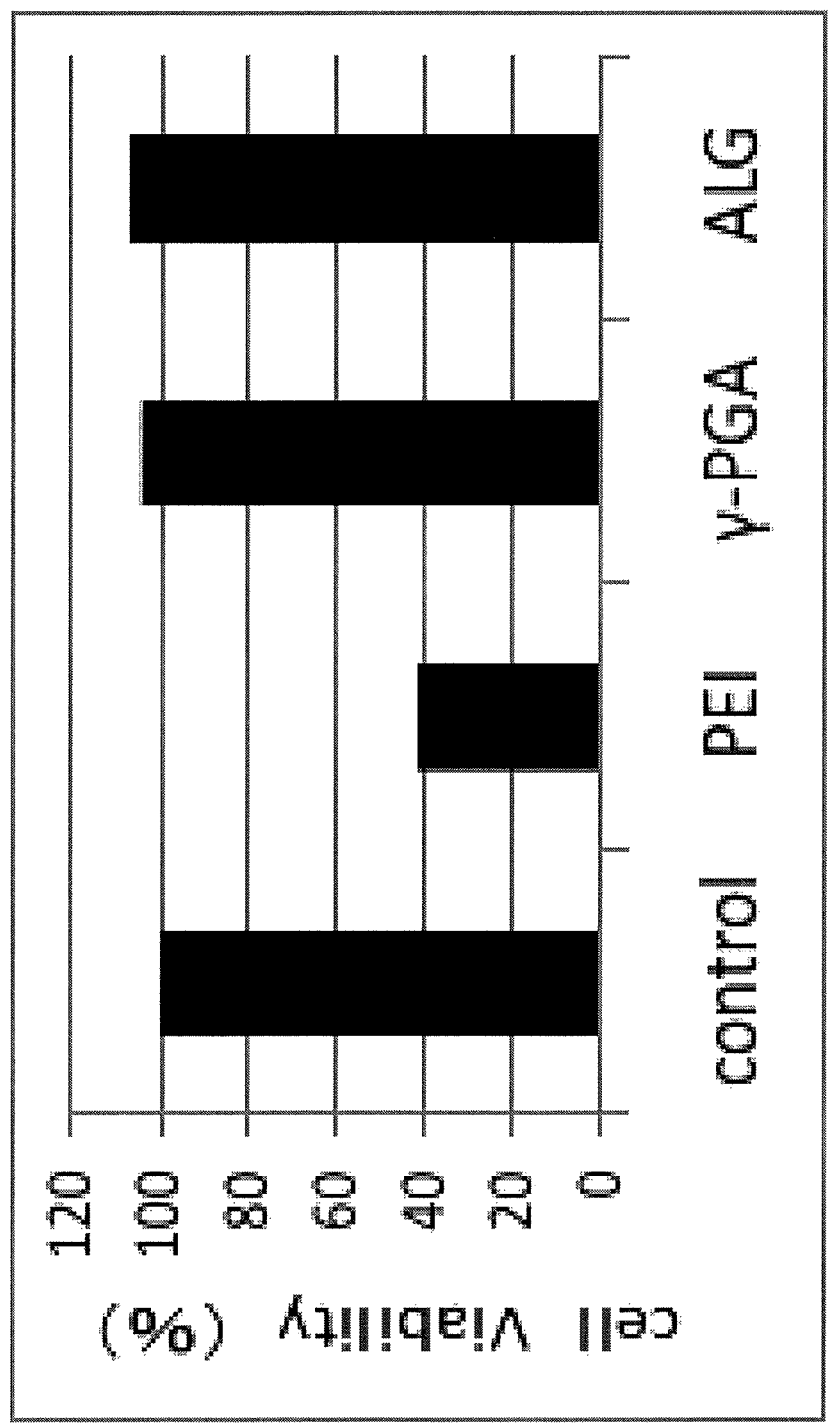
FIG. 23 shows cytotoxicity in Example 15.
Figure 24:
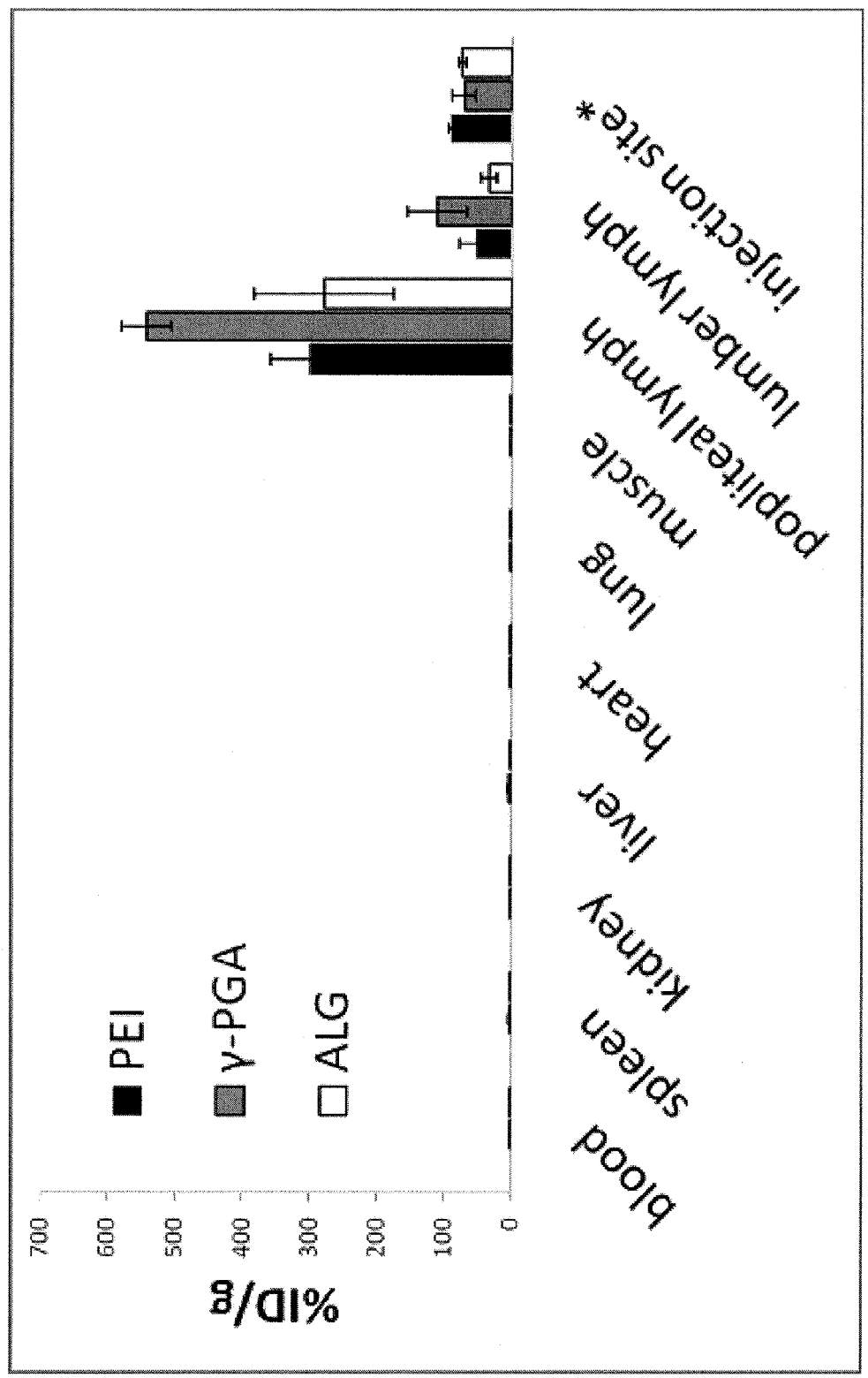
FIG. 24 shows distribution of the complex in vivo at 24 hr after administration to rat Foot Pad in Example 15.
Figure 25:
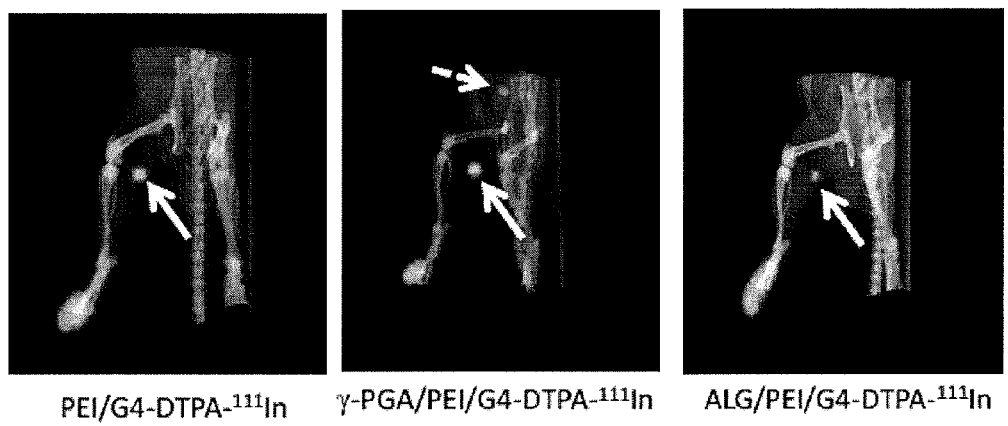
FIG. 25 shows SPECT/CT images at 24 hr after administration to rat Foot Pad in Example 15, wherein an arrow (solid line) shows popliteal lymph node and an arrow (dotted line) shows lumbar lymph node.

While PEI/G4-DTPA showed a highly strong cytotoxicity, γ-PGA/PEI/G4-DTPA and ALG/PEI/G4-DTPA did not show cytotoxicity (FIG. 23). Using mouse red blood cell, the red blood cell agglutination and hemolysis of each complex were evaluated. As a result, remarkable agglutination of red blood cell and slight hemolysis were confirmed with PEI/G4-DTPA, whereas agglutination of red blood cell and hemolysis were not observed with γ-PGA/PEI/G4-DTPA and ALG/PEI/G4-DTPA. Accumulation of γ-PGA/PEI/G4-DTPA-$^{111}$In in the sentinel lymph node at 24 hr after administration was significantly higher than other complexes. In any complex, the uptake in the sentinel lymph node and the organs other than the administration site showed very low values, which indicates that the leakage of each complex from the lymph vessel into the blood vessel does not occur easily (FIG. 24). Also, in SPECT/CT imaging, γ-PGA/PEI/G4-DTPA-$^{111}$In was highly accumulated in the sentinel lymph node as compared to other complexes, and clear imaging was successfully performed (FIG. 25).

INDUSTRIAL APPLICABILITY

The complex of the present invention does not cause red blood cell agglutination, shows low cytotoxicity, and is superior in the cellular uptake efficiency, it can deliver an antigen or drug safely and effectively.

Particularly, since the complex of the present invention is characteristically highly oriented to the target cell or organ, it can be an active ingredient of a new drug delivery system.

Moreover, the complex of the present invention can also be used as a carrier of an imaging probe.

This application is based on patent application No. 2010-043186 filed in Japan (filing date: Feb. 26, 2010), the contents of which are incorporated in full herein.

The invention claimed is:

1. A method of imaging a lymph node in a mammal, comprising
   (1) administering to the mammal a complex comprising
      (a) a drug complex consisting of a nuclide for imaging, a cationic dendrimer and a chelating agent;
      (b) polyethylenimine; and
      (c) γ-polyglutamic acid, and
   (2) imaging the lymph node in the mammal.

2. The method of claim 1, wherein the nuclide for imaging is (a) a radioactive nuclide for positron-emission tomography (PET) or compound labeled therewith, (b) a radioactive nuclide for single photon emission computed tomography (SPECT) or compound labeled therewith, (c) contrast agent for nuclear magnetic resonance imaging (MRI) or compound labeled therewith, (d) dye or compound labeled therewith, (e) fluorescent dye or compound labeled therewith, or (f) a compound that is a molecule probe or tracer.

3. The method of claim 1, wherein the cationic dendrimer is a polyamideamine dendrimer.

4. The method of claim 1, wherein the chelating agent is p-SCN benzyldiethylenetriamine pentaacetic acid (DTPA).

5. The method of claim 1, wherein the lymph node is a sentinel lymph node.

* * * * *